United States Patent
Thygesen et al.

(10) Patent No.: US 7,868,176 B2
(45) Date of Patent: *Jan. 11, 2011

(54) SALTS OF N-(4-FLUOROBENZYL)-N-(1-METHYL PIPERIDIN-4-Y1)-N'-(4-(2-METHYL PROPYLOXY)PHENYLMETHYL) CARBAMIDE AND THEIR PREPARATION

(75) Inventors: Mikkel Boas Thygesen, Copenhagen East (DK); Nathalie Schlienger, Frederiksberg (DK); Bo-Ragnar Tolf, Malmö (SE); Fritz Blatter, Reinach (CH); Jörg Berghausen, Lörrach (DE)

(73) Assignee: ACADIA Pharmaceuticals, Inc., San Diego, CA (US)

( * ) Notice: Subject to any disclaimer, the term of this patent is extended or adjusted under 35 U.S.C. 154(b) by 840 days.

This patent is subject to a terminal disclaimer.

(21) Appl. No.: 11/235,381

(22) Filed: Sep. 26, 2005

(65) Prior Publication Data

US 2006/0111399 A1  May 25, 2006

Related U.S. Application Data

(60) Provisional application No. 60/614,014, filed on Sep. 27, 2004.

(51) Int. Cl.
C07D 211/56 (2006.01)
A61K 31/47 (2006.01)

(52) U.S. Cl. ...................... 546/224; 514/317
(58) Field of Classification Search .................. 546/224; 514/317
See application file for complete search history.

(56) References Cited

U.S. PATENT DOCUMENTS

| | | |
|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,853,394 A | 8/1989 | King et al. |
| 5,025,013 A | 6/1991 | Barreau et al. |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda et al. |
| 5,707,798 A | 1/1998 | Brann |
| 5,795,894 A | 8/1998 | Shue et al. |
| 5,869,488 A | 2/1999 | Shue et al. |
| 5,877,173 A | 3/1999 | Olney et al. |
| 5,912,132 A | 6/1999 | Brann |
| 5,955,281 A | 9/1999 | Brann |
| 6,107,324 A | 8/2000 | Behan et al. |
| 6,140,509 A | 10/2000 | Behan et al. |
| 6,150,393 A | 11/2000 | Behan et al. |
| 6,214,846 B1 * | 4/2001 | Elliott ........................ 514/331 |
| 6,358,698 B1 | 3/2002 | Weiner et al. |
| 6,756,393 B2 | 6/2004 | Andersson et al. |
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 7,115,634 B2 | 10/2006 | Thurieau et al. |
| 2004/0006081 A1 | 1/2004 | Burrows et al. |
| 2004/0106600 A1 | 6/2004 | Andersson et al. |
| 2004/0213816 A1 * | 10/2004 | Weiner et al. ............ 424/239.1 |
| 2005/0014757 A1 | 1/2005 | Andersson et al. |
| 2005/0148018 A1 | 7/2005 | Weiner et al. |
| 2005/0192268 A1 * | 9/2005 | Ek et al. ................. 514/211.13 |
| 2005/0244862 A1 | 11/2005 | Brann |
| 2005/0256108 A1 | 11/2005 | Schlienger |
| 2005/0261340 A1 * | 11/2005 | Weiner et al. ................ 514/317 |
| 2005/0288328 A1 * | 12/2005 | Weiner et al. ................ 514/317 |
| 2006/0094758 A1 | 5/2006 | Andersson et al. |
| 2006/0106063 A1 * | 5/2006 | Thygesen et al. ............ 514/317 |
| 2006/0194778 A1 | 8/2006 | Andersson et al. |
| 2006/0194784 A1 * | 8/2006 | Ek et al. ................. 514/211.13 |
| 2006/0194834 A1 | 8/2006 | Andersson et al. |
| 2006/0199794 A1 | 9/2006 | Schlienger |
| 2006/0199818 A1 | 9/2006 | Andersson et al. |
| 2006/0199842 A1 | 9/2006 | Weiner et al. |
| 2006/0205710 A1 | 9/2006 | Schlienger et al. |
| 2006/0205722 A1 | 9/2006 | Andersson et al. |
| 2006/0205780 A1 * | 9/2006 | Thygesen et al. ............ 514/317 |

(Continued)

FOREIGN PATENT DOCUMENTS

CA    984843    3/1978

(Continued)

OTHER PUBLICATIONS

Berge et al J. Pharm. Sci. 1977, 66, 1-19.*

(Continued)

*Primary Examiner*—Janet L Andres
*Assistant Examiner*—John Mabry
(74) *Attorney, Agent, or Firm*—Jones Day

(57) ABSTRACT

Disclosed herein are salts of N-(4-fluorobenzyl)-N-(1-methylpiperidin-4-yl)-N'-(4-(2-methylpropyloxy) phenylmethyl) carbamide including the citrate, fumarate, maleate, malate, phosphate, succinate, sulphate, and edisylate salts.

16 Claims, 5 Drawing Sheets

U.S. PATENT DOCUMENTS

| | | | |
|---|---|---|---|
| 2006/0205781 A1* | 9/2006 | Thygesen et al. | 514/317 |
| 2006/0264465 A1 | 11/2006 | Weiner et al. | |
| 2006/0264466 A1* | 11/2006 | Weiner et al. | 514/317 |
| 2006/0286610 A1 | 12/2006 | Brann | |
| 2006/0292606 A1 | 12/2006 | Brann | |
| 2007/0260064 A1* | 11/2007 | Tolf et al. | 546/224 |

FOREIGN PATENT DOCUMENTS

| | | |
|---|---|---|
| EP | 0 005 318 A1 | 11/1979 |
| EP | 0 061 333 A1 | 9/1982 |
| EP | 0 379 441 A1 | 7/1990 |
| EP | 0 548 015 A1 | 6/1993 |
| EP | 0 260 070 B1 | 8/1993 |
| EP | 0 625 507 A2 | 11/1994 |
| FR | 2802206 A1 | 6/2001 |
| HU | 157325 | 3/1998 |
| WO | WO 94/27967 A1 | 12/1994 |
| WO | WO 97/08166 A1 | 3/1997 |
| WO | WO 97/11940 A1 | 4/1997 |
| WO | WO 97/38665 A2 | 10/1997 |
| WO | WO 97/38984 A1 | 10/1997 |
| WO | WO 98/11128 A1 | 3/1998 |
| WO | WO 98/17646 A1 | 4/1998 |
| WO | WO 98/44921 A1 | 10/1998 |
| WO | WO 98/50534 A1 | 11/1998 |
| WO | WO 99/52927 A1 | 10/1999 |
| WO | WO 00/23076 A1 | 4/2000 |
| WO | WO 00/56335 A1 | 9/2000 |
| WO | WO 00/59497 A1 | 10/2000 |
| WO | WO 00/69810 A1 | 11/2000 |
| WO | WO 01/44191 A1 | 6/2001 |
| WO | WO 01/66521 A1 | 9/2001 |
| WO | WO 01/87839 A1 | 11/2001 |
| WO | WO 02/079186 A2 | 10/2002 |
| WO | WO 03/057698 A2 | 7/2003 |
| WO | WO 03/057698 A3 | 7/2003 |
| WO | WO 03/062206 A2 | 7/2003 |
| WO | WO 03/062208 A3 | 7/2003 |
| WO | WO 03/070246 A1 | 8/2003 |
| WO | WO 03/086400 A1 | 10/2003 |
| WO | WO 2004/000808 A2 | 12/2003 |
| WO | WO 2004/000808 A3 | 12/2003 |
| WO | WO 2004/009549 A2 | 1/2004 |
| WO | WO 2004/039322 A2 | 5/2004 |
| WO | WO 2004/064738 * | 8/2004 |
| WO | WO 2004/064738 A2 | 8/2004 |
| WO | WO 2004/064753 * | 8/2004 |
| WO | WO 2004/064753 A2 | 8/2004 |
| WO | WO 2004/072034 A1 | 8/2004 |
| WO | WO 2004/084738 A3 | 8/2004 |
| WO | WO 2005/063254 A2 | 7/2005 |
| WO | WO 2005/112927 A | 12/2005 |
| WO | WO 2006/036874 A1 | 4/2006 |
| WO | WO 2006/037043 A1 | 4/2006 |

OTHER PUBLICATIONS

T.W. Graham Solomons and Craig B. Fryhle "Organic Chemistry" 9th Edition, John Wiley & Sons, Inc. 2008, pp. 903-909.*
Cox, R., "Medicinal Chemistry- 28th International Symposium: Jun. 8-12, 2002, San Diego, CA, USA," *IDrugs*, vol. 5, No. 7, pp. 626-632 (2002).
Johnston et al., "Drugs in Development for Parkinson's Disease: An Update," *Current Opin. Investig. Drugs*, vol. 7, No. 1, pp. 25-32 (2006).
Maubach, K., "Psychiatric Drug Discovery and Development," *Expert Opin. Investig. Drugs*, vol. 12, No. 9, pp. 1571-1575 (2003).
Meltzer et al., "Serotonin Receptors: Their Key Role in Drugs to Treat Schizophrenia," *Progress in Neuro-Pyschopharmacology & Biol. Psych.*, vol. 27, pp. 1159-1172 (2003).
Morgan et al., "Emerging Drugs for Parkinson's Disease," *Expert Opin. Emerging Drugs.*, vol. 11, No. 3, pp. 403-417(2006).
Roberts, C. "Drug Evaluation: ACP-103, a 5-HT2A Receptor Inverse Agonist," *Current Opin. Investig. Drugs*, vol. 7, No. 7, pp. 653-660 (2006).
Vanover et al., "ACP-103, A 5-HT2A Receptor Inverse Agonist, A Novel Potential Treatment For Psychosis," *Schizophrenia Research*, vol. 60, No. 1, Supp. [S], p. 317 (2003).
Vanover et al., "ACP-103, A 5-HT2A Receptor Inverse Agonist: Safety, Tolerability and Pharmacokinetics in Healthy Volunteers," *International J. Neuropsychopharmacology*, vol. 7, No. Supp. 2, pp. S253 (2004).
Vanover et al., "Pharmacological and Behavioral Profile of N-(4-fluorophenylmethyl)-N-(1-methylpiperidin'4-yl)-N'-(4-(2-methylpropyloxy)phenylmethyl) Carbamide (2R, 3R)-Dihydroxybutanedioate (2:!) (ACP-103), a Novel 5-Hydroxytrptamine 2A Receptor Inverse Agonist," *J. Pharmacology & Experimental Therapeutics*, vol. 317, No. 2, pp. 910-918 (2006).
R & D Focus Drug News, vol. 10, No. 44, pp. 1-6 (Nov. 12, 2001).
Office Action dated Jan. 6, 2009 in U.S. Appl. No. 10/759,561.
Declaration of Dr. Douglas W. Bonhaus, filed Oct. 14, 2008 in U.S. Appl. No. 10/759,561.
Office Action dated Jul. 11, 2008 in U.S. Appl. No. 10/759,561.
Office Action dated Oct. 10, 2007 in U.S. Appl. No. 10/759,561.
Office Action dated Jan. 15, 2009 in U.S. Appl. No. 11/235,558.
Office Action dated Jan. 22, 2009 in U.S. Appl. No. 11/417,447.
Acadia Pharmaceuticals Announces Results from Phase III Trial of Pimavanserin in Parkinson's Disease Psychosis, *Press Release (Business Wire*, San Diego), Sep. 1, 2009.
Acadia Pharmaceuticals Provide Update on Pimavanserin Collaborative Development Program, *Press Release (Business Wire*, San Diego), Oct. 6, 2009.
Jones et al., "Pharmaceutical Cocrystals: An Emerging Approach to Physical Property Enhancement," *Mater. Res. Bull.*,31:875-79 (2006).
Andrew D. Bond & William Jones, Controlling Crystal Architecture in Molecular Solids: The Supramolecular Approach, in Supramolecular Organization and Materials Design, 391, 436 (W. Jones & C. N. R. Rao, eds., 2001).
Notice of Allowance dated Jun. 17, 2009 in U.S. Appl. No. 10/759,561.
Caroon, et al. 1981. Synthesis and anatypertensive activity of a series of 8-substituted 1-Oxa-3,8-diazaspiro[4.5]decan-2-ones. *J. Med. Chem.*, 24:1320-1328.
Chemical Abstracts, 73:25305. Benke, et al. 1970.
Clifton, et al. 1982. Arylethanolamines Derived from Salicyclamide with α- and β- Adrenoceptor Blocking Activities. Preparation of Labetalol, its Enantiomers, and Related Salicyclamides. *J. Med. Chem.*, 25:670-679.
Delecluse, et al. 1998. A case of tardive tremor successfully treated with clozapine. *Movement Disorders*, 13(5):846-847.
Factor, et al. 1992. Clozapine prevents recurrence of psychosis in Parkinson's disease. *Movement Disorders*, 7(2):125-131.
Factor, et al. 2001. Clozapine for the treatment of drug-induced psychosis in Parkinson's disease: Results of the 12 week open label extension in the PSYCLOPS trial. *Movement Disorders*, 16(1):135-139.
Friedman, J. H. 1994. Clozapine treatment of psychosis in patients with tardive dystonia: Report of three cases. *Movement Disorders*, 9(3):321-324.
Harper, et al. 1964, The chemistry and pharmacology of some 4-aminoplperidines and their derivatives.*J. Med. Chem.*, 44:729-732.
Herrick-Davis, et al. 2000. Inverse agonist activity of atypical antipsychotic drugs at human 5-hydroxyhyptarnine2C receptors. *The Journal of Pharmacology and Experimental Therapeutics*, 295(1):226-232.
Kalgutkar, et al. 1995. Selective inhibitors of monoamine oxidase (MAO-A and MAO-B) as probes of its catalytic site and mechanism. *Medicinal Research Reviews*, 15(4)325-388. XP002034298.
Möehrle, et al. 1990. Sodium mercury edetate dehydrogenation of N-aliphatic substituted 1,2,3,6-tetrahydropyridine derivatives. *Arch. Pharm. (Weinheim)*, 323:109-115.

Smith, et al. 1995. New spiroplperdines as potent and selective non-peptide tachykinin NK$_2$receptor antagonists. *J. Med. Chem.*, 38(19):3772-3779.

Wade, et al. 2000. Application of base cleavable safety catch linkers to solid phase library production. *J. Comb. Chem.*, 2(3):266-275.

Yoshida. et al. 1998 Marked improvement of tardive dystonia after replacing haloperidol with risperidone in a schizophrenic patient. *Clinical Neuropharmacology*, 21(1):68-69.

Notice of Allowance and Fee(s) Due and Notice of Allowability dated May 15, 1997, from U.S. Appl. No. 08/273,859, filed Jul. 12, 1994, now U.S. Pat. No. 5,707,798.

Office Action dated Mar. 27, 1998, from U.S. Appl. No, 08/954,724, filed Oct. 20, 1997, now U.S. Pat. No. 5,912,132.

Notice of Allowance and Fee(s) Due and Notice of Allowability dated Sep. 4, 1998, from Application No. 08/954,724 filed Oct. 20, 1997, now U.S. Pat. No. 5,912,132.

Office Action dated Sep. 14, 1998, from U.S. Appl. No. 08/965,947, filed Nov. 7, 1997, now U.S. Pat. No. 5,955,281.

Interview Summary dated Nov. 17, 1908, from U.S. Appl. No. 08/965,947, filed Nov. 7, 1997, now U.S. Pat. No. 5,955,281.

Office Action dated Apr. 25, 2002, from U.S. Appl. No. 09/800,096, now U.S. Pat. No. 6,815,458.

Office Action dated Jan. 21, 2003, from U.S. Appl. No. 09/800,096, now U.S. Pat. No. 6,815,458.

Office Action dated Jul. 15, 2003, from U.S. Appl. No. 09/800,096, now U.S. Pat. No. 6,815,458.

Notice of Allowability dated Dec. 8, 2003, from U.S. Appl. No. 09/800,096, filed Mar. 6, 2001, now U.S. Pat No. 6,815,458.

Notice of Allowance and Fee(s) Due and Notice of Allowability dated Dec. 5, 2003, from U.S. Appl. No. 10/409,782, filed Apr. 7, 2003, now U.S. Pat. No. 8,758,393.

International Preliminary Examination Report dated Mar. 18, 2003, for PCT/US01/07187.

International Search Report dated Jul. 17, 2001 for PCT/US01/07187.

Written Opinion dated Nov. 22, 2002 for PCT/US01/07187.

Office Action dated Feb. 28, 2001, from U.S. Appl. No. 09/413,626, filed Oct. 6, 1999, now U.S. Pat. No. 6,358,698.

Notice of Allowance and Fee(s) Due and Notice of Allowability dated Nov. 20, 2001, from U.S. Appl. No. 09/413,626, filed Oct. 6, 1999, now U.S. Pat. No. 6,358,698.

Office Action dated May 21, 2004, from U.S. Appl. No. 10/329,719, filed Dec. 23, 2002, now U.S. Pat. No. 6,911,452.

Notice of Allowance and Fee(s) Due and Notice of Allowability dated Feb. 11, 2005, from U.S. Appl. No. 10/329,719, filed Dec. 23, 2002, now U,S, Pat. No. 6,911,452.

Office Action dated Jan. 17, 2006, from U.S. Appl. No. 11/154,083, filed Jun. 16, 2005.

Office Action dated Jun. 26, 2006, from U.S. Appl. No. 11/154,083, filed Jun. 16, 2005.

Notice of Allowability, Notice of Allowance and Fee(s) Due, and Interview Summary dated Dec. 15, 2006, from U.S. Appl. No. 11/154,083, filed Jun. 16, 2005.

Office Action dated Oct. 5, 2006, from U.S. Appl. No. 11/418,322, filed May 3, 2006.

Office Action dated Jan. 23, 2007, from U.S. Appl. No. 11/418,322, filed May 3, 2006.

International Search Report dated May 8, 2003 for PCT/US02/41476.

Written Opinion dated Sep. 9, 2003, for PCT/US02/41476.

International Preliminary Examination Report dated Jan. 15, 2004, for PCT/US02/41476.

Office Action dated Nov. 4, 2004, from U.S. Appl. No. 10/601,070, filed Jun. 20, 2003.

Notice of Allowance and Fee(s) Due and Notice of Allowability dated Jul. 12, 2006, from U.S. Appl. No. 10/601,070, filed Jun. 20, 2003.

Notice of Allowance and Fee(s) Due and Notice of Allowability dated Mar. 29, 2006, from U.S. Appl. No. 10/601,070, filed Jun. 20, 2003.

International Search Report dated Dec. 3, 2003, for PCT/US03/19797.

Written Opinion for PCT/US03/19797 dated Apr. 5, 2004.

International Preliminary Examination Report dated Jul. 28, 2004 for PCT/US03/19797.

International Search Report dated Sep. 8, 2004, for PCT/US2004/001234.

International Written Opinion dated Sep. 8, 2004, for PCT/US2004/001234.

International Preliminary Report on Patentability dated Apr. 14, 2005, for PCT/US2004/001234.

International Search Report dated Jan. 30, 2006, for PCT/US2005/034813.

Written Opinion of the International Searchrng Authority dated Jan. 30, 2006, for PCT/US2005/034813.

International Search Report dated Jan. 30, 2006, for PCT/US2005/034376.

Written Opinion of the International Searching Authority dated Jan. 30, 2006, or PCT/US2005/034376.

Office Action dated Feb. 5, 2007, from U.S. Appl. No. 11/229,566, filed Dec. 12, 2005.

Ryckmans, et al. 2002. First dual NK1 antagonists—serotonin reuptake inhibitors: synthesis and SAR of a new class of potential antidepressants. *Biorganic & Medicinal Chemistry Letters* 12:261-264.

Thomas, et al. 1997. "Rapid in-plate generationof benzimidazole libraries and amide formation using EEDQ," *Tetrahedron Lett.* 39(29):5099-5102.

Office Action dated Oct. 22, 2007 from U.S. Appl. No. 11/417,782, filed May 3, 2006.

Office Action dated Oct. 12, 2007 from U.S. Appl. No. 11/417,439, filed May 3, 2006.

Office Action dated Oct. 2, 2007, from U.S. Appl. No. 11/299,566, filed Dec. 12, 2005.

Office Action dated Oct. 26, 2007, from U.S. Appl. No. 11/417,866, filed May 3, 2006.

Office Action dated Oct. 10, 2007, from U.S. Appl. No. 10/759,561, filed Jan. 15, 2004.

Office Action dated Jan. 30, 2008, from U.S. Appl. No. 11/417,790, filed May 3, 2006.

Office Action dated Jan. 25, 2008, from U.S. Appl. No. 10/802,970, filed Mar. 16, 2004.

Notice of Allowance and Fee(s) Due and Notice of Allowability dated Feb. 19, 2008, from U.S. Appl. No. 11/417,439, filed May 3, 2006.

Office Action dated Dec. 17, 2007, from U.S. Appl. No. 11/299,566, filed Dec. 12, 2005.

Office Action dated Feb. 22, 2008, from U.S. Appl. No. 11,417,866, filed May 3, 2006.

Office Action dated Mar. 28, 2008, from U.S. Appl. No. 11/417,782, filed May 3, 2006.

Office Action dated Jul. 14, 2006, from U.S. Appl. No. 10/601,070, filed Jun. 20, 2003.

Supplemental Notice of Allowability dated May 23, 2008, from U.S. Appl. No. 11/417,439, filed May 3, 2006.

Adam, et al. 1989. Effects of repeated ritanserin on middle-aged poor sleepers. *Psychopharmacology*, 99:219-221.

Adell, et al. 2005. Strategies for producing faster acting antidepressants. *Drug Discovery Today*, 10(8):578-585.

Akin, et al. 2004. Decreased serotonin 5-HT$_{2A}$ receptor-stimulated phosphoinositide signaling in fibroblasts from melancholic depressed patients. *Neuropsychopharmacology*, 29:2081-2087.

Alvisi, N. 1892. Sulla formazione di derivati pirazolici dalle dicloridrine e dalle tribromidrina della glicerina ordinaria, *Gazz. Chem. Ital*, 22:158-168.

Antilla, et al. 2001. Copper-catalyzed coupling of arylboronic acids and amines. *Organic Letters*, 3(13):2077-2079.

Antilla, et al. 2002. The copper-catalyzed N-arylation of indoles. *J. Am. Chem. Soc.*, 124:11684-11688.

Archibald, et al., 1974 "Benzamidopiperdines. 2. Heterocyclic Compounds Related to Indoramin" *J. Medicinal Chemistry*, 17(7):736-739.

Archibald, et al., 1974 "Benzamidopiperdines. 3. Heterocyclic Compounds Related to Indoramin" *J. Medicinal Chemistry*l, 17(7):-739-744.

Archibald, et al., 1974 "1,4-Bis-(2-indo1-3-ylethyl)piperdines" J. Medicinal Chemistry, 17(7):-745-747.

Artico, et al. 1992. Aromatic hydrazides as specific inhibitors of bovine serum amine oxidase, *Eur. J. Med. Chem.*, 27:219-228.

Bakshi, et al. 1994. Clozapine antagonizes phencyclidine-induced deficits in sensorimotor gating of the startle response. *The Journal of Pharmacology and Experimental Therapeutics*, 271(2):787-794.

Barchas, J. 1973. *Serotonin and Behavior*. New York: Academic Press.

Barnes, et al. 1999. A review of central 5-HT receptors and their function. *Neuropharmacology*, 38:1083-1152.

Barr, et al. 1997. Agonist-independent activation of $G_z$ by the 5-hydroxytryptamine$_{1A}$ receptor co-expressed in *Spodoptera frugiperda* cells, *The Journal of Biological Chemistry*, 272(52):32979-32987.

Bassus, et al. 1974. Psychotropes potentiels. X. Synthèse de butyrophénones à cycle pipéridine-spiro-tétrahydrooxazinane douées d'activité neuroleptique. *Eur. J. Med Chem.—Chimica Therapeutica*, 9(4):416-423.

Bennett, et al. 1993. Suppression of dyskinesias in advanced Parkinson's disease. II. Increasing daily clozapine doses suppress dyskinesias and improve parkinsonism symptoms. *Neurology*, 43:1551-1555.

Bhatia, et al. 1996. 5-Lipoxygenase inhibitors: Synthesis and structure-activity relationships of a series of 1-Aryl-2*H*,4*H*-tetrahydro-1,2,4--triazin-3-ones. *J. Med. Chem.*, 39:3938-3950.

Biagi, et al. 1988. 1,2,3-Triazoles: Structural changes on two effective inhibitors of the prostaglandin synthesis in vitro. *Farmaco Ed. Sci.*, 43:597-612.

Bibbiani, et al. 2001. Serotonin 5-HT1A agonist improves motor complications in rodent and primate parkinsonian models. *Neurology*, 57:1829-1834.

Birkmayer, et al. 1974. Nucleus ruber and L-Dopa psychosis: Biochemical post-mortem findings. *Journal of Neural Transmission*, 35:93-116.

Blakley, et al. 2001. Bidirectional changes in ethanol consumption in rats with site-specific antisense down-regulation of 5-hydroxytryptamine$_{2A}$ receptors in brain. *The Journal of Pharmacology and Experimental Therapeutics*, 299(1):277-289.

Blier, et al. 2001. Putative mechanisms of action of antidepressant drugs in affective and anxiety disorders and pain. *Journal of Psychiatry & Neuroscience*, 26(1):37-43.

Blier, et al. 2005. Potential mechanisms of action of atypical antipsychotic medications in treatment-resistant depression and anxiety. *J. Clin. Psychiatry*, 66(suppl 8):30-40.

Bond, et al. 1995. Physiological effects of inverse agonists in transgenic mice with myocardial overexpression of the $\beta_2$-adrenoceptor. *Nature*, 374:272-276.

Boullin, D. J. 1978. *Serotonin in Mental Abnormalities* (p. 316). New York: Wiley.

Brown, et al. 1924. Catalytic alkylation of aniline, *J. Am. Chem. Soc.*, 46(8):1836-1839.

Büchi, et al. 1969. Synthesis of (±)-nuciferal. *J. Org. Chem.*, 34(4):1122-1123.

Butcher, et al. 1970. L-Dopa induced changes in central monoamine neurons after peripheral decarboxylase inhibition. *Letters to the Editor, J. Pharm. Pharmac.*, 22:313-316.

Buu-Hoï, et al. 1951. Further studies in the alkylation of phenols and thiophenols, *J. Org. Chem.*, 16:988-994.

Cacchi, et al. 2003. Palladium-catalyzed reaction of aryl iodides with acetic anhydride. A carbon monoxide-free synthesis of acetophenones. *Organic Letters*, 5(3):289-291.

Carman, et al. 1998. A further synthesis of an analogue of the antifungal/antiherbivore lipid from avocado. *Aust. J. Chem.*, 51:955-959.

Carroll, et al. 1992. Synthesis and muscarinic receptor activity of ester derivatives of 2-substituted 2-azabicyclo[2.2.1]heptan-5-ol and -6-ol. *J. Med. Chem.*, 35:2184-2191.

Catarzi, et al. 2001. Synthesis, ionotropic glutamate receptor binding affinity, and structure-activity relationships of a new set of 4,5-dihydro-8-heteroaryl-4-oxo-1,2,4-triazolo[1,5-a]quinoxaline-2-carboxylates analogues of TQX-173. *J. Med Chem.*, 44:3157-3165.

Cerione, et al. 1984. The mammalian $\beta_2$-adrenergic receptor: Reconsitution of functional interactions between pure receptor and pure stimlatory nucelotide binding protein of the adenylate cyclase system. *Biochemistry*, 23:4519-4525.

Chemical Abstracts, 128:111548. Brann, M. R. 1998. Identification of ligands by selective amplification of cells transfected with receptors and marker enzymes.

Cherkasov, et al. 1985. Organothiophosphorus reagents in organic synthesis. *Tetrahedron*, 41 (13):2567-2624.

Clark et al. 1983. Antihypertensive 9-substituted 1-Oxa-4,9-diazaspiro[5.5]undecan-3-ones. *J. Med. Chem.*, 26:855-861.

DeClerck, et al. 1987. Increase in slow-wave sleep in humans with the serotonin-$S^2$ antagonist ritanserin. Current Therapeutic Research, 41(4):427-432.

Dunn, et al. 1986. Analgetic and antiinflammatory 7-aroylbenzofuran-5-ylacetic acids and 7-aroylbenzothiophene-5-ylacetic acids. *J. Med. Chem.*, 29:2326-2329.

Durif, et al. 1997. Low-dose clozapine improves dyskinesias in Parkinson's disease. *Neurology*, 48:658-662.

Eichelbaum, et al. 1996. Influence of pharmacogenetics on drug disposition and response. *Clinical and Experimental Pharmacology and Physiology*, 23:983-985.

Emerson, et al. 1938. The reductive alkylation of aniline. *J. Am. Chem. Soc.*, 60 2023-2025.

Ermakov, et al. 1981. Use of Mass spectrometry in structural and stereochemical studies. *Chemistry of Heterocyclic Compounds*, 1:72-77.

Everett, et al. 1970. L-Dopa: Effect on concentrations of dopamine, norepinephrine, and serotonin in brains of mice. *Science*, 168:849-850.

Finar, et al. 1954. The preparation and properties of some derivatives of 1-phenylpyrazole, *J. Chem. Soc.*, pp. 2293-2298.

Fišera, et al. 1994. Synthesis of spiro-substituted 1,3-oxazines by a new sequence leading to spiroheterocycles. *Monatshefte für Chemie*, 125:909-919.

Friedman, et al. 1999. Low-dose clozapine for the treatment of drug-induced psychosis in Parkinson's disease. *N. Engl. J. Med.*, 340(10):757-763.

Friedman, et al. 2000. Atypical antipsychotics in the treatment of drug-induced psychosis in Parkinson's disease. *Movement Disorders*, 15(2):201-211.

Fuller, R. W. 1982. Drugs acting on serotonergic neuronal systems. In N. N. Osborne (Ed.), *Biology of Serotonergic Transmission*, Chap. 9, pp. 221-247. New York: Wiley.

Gainetdinov, et al. 2001. Genetic animal models: Focus on schizophrenia. *Trends in Neurosciences*, 24(9)527-533.

Gamma, et al. 2000. 3,4-Methylenedioxymethamphetamine (MDMA) modulates cortical and limbic brain activity as measured by [$H_2^{15}O$]-PET in healthy humans. *Neuropsychopharmacology*, 23(4):388-395.

Gawley, R. E., & Aubé, J. 1996. *Principles of Asymmetric Synthesis*. New York Pergamon.

Gershon, M. D., Mawe, G. M., & Branchek, T. A. 1989. 5-Hydroxytryptamine and enteric neurones. In J. R. Fozard (Ed.), *The Peripheral Actions of 5-Hydroxytryptamine* (pp. 247-273). New York: Oxford University Press.

Gillman, P. K. 2005. Monoamine oxidase inhibitors, opioid analgesics and serotonin toxicity. *British Journal of Anaesthesia*, 95(4):434-441.

Glennon, R. A. 1990. Serotonin receptors: Clinical implications. *Neuroscience & Biobehavioral Reviews*, 14:35-47.

Gooβen, et al. 2001. Palladium-catalyzed synthesis of aryl ketones from boronic acids and carboxylic acids or anhydrides. *Angew. Chem. Int. Ed.*, 40:3458-3460.

Gstach, et al. 1990. Rearrangement of 3,3-disubstituted 1-aryl-4,5-dihydro-5oxo-3*H* 1,2,4-triazolium tetrafluoroborates; Part 1. A versatile synthesis of 1,5-disubstituted 2-aryl-1,2-dihydro-3*H* -1,2,4-triazol-3-one tetrafluoroborates. *Synthesis*, pp. 803-808.

Guthrie, et al. 1993. The tetrahedral intermediate form the hydration of *N* methylformanihde. *Can. J. Chem.*, 71:2109-2122.

Hartwig, J. F. 1998. Transition metal catalyzed synthesis of arylamines and aryl ethers from aryl halides and triflates: Scope and mechanism. *Angew. Chem. Int. Ed.*, 37 2047-2067.

Hickinbottom, W. J. 1930. The preparation of secondary alkylarylamines and their purification. *J. Chem. Soc.*, pp. 992-994.

Hirst, et al. 1895. A method for preparing the formyl derivatives of the aromatic amines. *J. Chem. Soc.*, 67:829-831.

Idzikowski, et al. 1991. A dose response study examining the effects of ritanserin on human slow wave sleep. *Br. J. Clin. Pharmac.*, 31:193-196.

Irikura et al., 1971 "New Anticulcer Agents. 1. Synthesis and Biological Activities of 1-Acyl-2,3-, -4-substituted Benzamidopiperdines" *J. Medicinal Chemistry* 14(4): 357-361.

Jaeger, et al. 1941. Two ketones of the stilboestrol group. *J. Chem, Soc.*, 744-747.

Julius, et al. 1990. The 5HT2 receptor defines a family of structurally distinct but functionally conserved serotonin receptors. *Proc. Natl. Acad. Sci. USA*, 87:928-932.

Kanayama, et al. 2005. New treatment of lumbar disc herniation involving 5-hydroxytryptamine$_{2A}$ receptor inhibitor: A randomized controlled trial. *J. Neurosurg: Spine*, 2:441-446.

Klapars, et al. 2001. A general and efficient copper catalyst for the amidation of aryl halides and the N-arylation of nitrogen heterocycles. *J. Am. Chem. Soc.*, 123:7727-7729.

Klapars, et al. 2002. A general and efficient copper catalyst for the amidation of aryl halides. *J. Am. Chem. Soc.*, 124:7421-7428.

Kuehne, et al. 1991(a). Enantioselective syntheses of vinblastine, leurosidine, vincovaline, and 20'-*epi*-vincovaline. *J. Org. Chem.*, 56(2):513-528.

Kuehne, et al. 1991(b). Total syntheses of *Yohimbe* alkaloids, with stereoselection for the normal, allo, and 3-epiallo series, based on annelations of 4-methoxy-1,2-dihydropyridones. *J. Org. Chem.*, 56(8):2701-2712.

Kwong, et al. 2002(a). Copper-catalyzed coupling of alkylamines and aryl iodides: An efficient system even in an air atmosphere. *Organic Letters*, 4(4):581-584.

Kwong, et al. 2002(b). A general, efficient, and inexpensive catalyst system for the coupling of aryl iodides and thiols. *Organic Letters*, 4(20):3517-3520.

Kwong, et al. 2003. Mild and efficient copper-catalyzed amination of aryl bromides and primary alkylamines. *Organic Letters*, 5(6):793-796.

Landini, et al. 1974. A convenient synthesis of primary and secondary dialkyl and aryl alkyl sulfides in the presence of phase-transfer catalysts. *Synthesis*, pp. 565-566.

Landolt, et al. 1999. Serotonin-2 receptors and human sleep: Effect of a selective antagonist on EEG power spectra. *Neuropsychopharmacology*, 21(3):455-466.

Leysen, et al. 1978. Serotonergic component of neuroleptic receptors. *Nature*, 272:168-171.

Li, G. Y. 2002. Highly active, air-stable palladium catalysts for the C-C and C-S bond-forming reactions of vinyl and aryl cholrides: Use of commercially available [(t -Bu)$_2$ P(OH)]$_2$ PdCl$_2$ [(t-Bu)$_2$ P(OH)PdCl$_2$ ]$_2$ and [[9t -Bu)$_{2 PO...H...OP}$(t -Bu)$_2$ ]PdCl]$_{2\ as\ catalysts}$. *J. Org. Chem.*, 67:3643-3650.

Liechti, et al. 2001. Effects of MDMA (ecstasy) on prepulse inhibition and habituation of startle in humans after pretreament with Citalopram, Haloperidol, or Ketanserin. *Neuropsychopharmacology*, 24(3):240-252.

Linder, et al. 1997. Pharmacogenetics: A laboratory tool for optimizing therapeutic efficiency. *Clinical Chemistry*, 43(2):254-266.

Lowe, et al. 1994. Aza-tricyclic substance P antagonists. *J. Med. Chem.*, 37:2831-2840.

Mansbach, et al. 1988. Dopaminergic stimulation disrupts sensorimotor gating in the rat. *Psychopharmacology*, 94:507-514.

Marek, et al. 2003. Synergistic action of 5-HT$_{2A}$ antagonists and selective serotonin reuptake inhibitors in neuropsychiatric disorders. *Neuropsychopharmacology*, 28:402-412.

Marek, et al. 2005. The selective 5-HT$_{2A}$ receptor antagonist M100907 enhances antidepressant-like behavioral effects of the SSRI fluoxetine. *Neuropsychopharmacology*, 30:2205-2215.

Mavunkel, et al. 1996. Synthesis and characterization of pseudopeptide bradykinin B2 receptor antagonists containing the 1,3,8-triazaspiro[4.5]decan-4-one ring system. *J. Med. Chem.*, 39:3169-3173.

Mayer, et al. 2003. Ritanserin improves sleep quality in narcolepsy. *Pharmacopsychiatry*, 364:150-155.

Meltzer, et al. 1995. Plasma clozapine levels and the treatment of L-DOPA-Incuced psychosis in Parkinson's disease. *Neuropsychopharmacology*, 12(1):39-45.

Meltzer, H. Y. 1999. The role of serotonin in antipsychotic drug action. *Neuropsychopharmacology*, 21(2S):106S-115S.

Meng, et al. 1991. Synthetic approaches toward glidobamine, the core structure of the glidobactin antibiotics. *Tetrahedron*, 47(32):62510-6264.

Mićovič, et al. 1991. A simple method for preparation of secondary aromatic amines. *Synthesis*, 11:1043-1045.

Miyata, et al. 2000. Sarpogrelate, a selective 5-HT$_{2A}$ serotonergic receptor antagonist, inhibits serotonin-induced coronary artery spasm in a porcine model. *Journal of Cardiovascular Pharmacology*, 35(2) 294-301.

Moulignier, A. 1994. Récepteurs centraux de la sérotonine principaux aspects fondamentaux et fonctionnels application therapeutiques. Rev. Neuroi., 150:3-15.

Moulignier, A. 1994. Récepteurs centraux de la sérotonine principaux aspects fondamentaux et fonctionnels application thërapeutiques. *Rev. Neurol.*, 150:3-15.

Moun, et al. 1997. Total synthesis of dolatrienoic acid: A subunit of dolastatin 14. *J. Org. Chem.*, 62:3332-3339.

Mullen et al. 2000. (-)-Spiro[1-azabicyclo[2.2.2]octane-3,5'-oxazolidin-2'one], a conformationally restricted analogue of acetylcholine, is a highly selective full agonist at the a7 nicotinic acetylcholine receptor. *J. Med. Chem.*, 43:4045-4050.

Muri, et al. 1998. Synthesis of new benzylic ethers of oximes derived from 1-phenyl-pyrazole compounds. *Synthetic Communications*, 28(7):1299-1321.

Ng, et al. 1970. L-dopa-induced release of cerebral monoamines. *Science*, 170:76-77.

Nigam, et al. 1957a. Studies with acetylenes. Part II. Some reactions of Grignard reagents with propargylic halides. Model Linoleic and Linolenic acid systems. *J. Chem Soc.*, pp. 3868-3873.

Nigam, et al. 1957b. The conversion of fatty acids into aldehydes. *J. Chem. Soc.*, pp. 3320- 3321.

Nordstrom, et al. 1993. High 5-HT$_2$ receptor occupancy in clozapine treated patients demonstrated by PET. *Psychopharmacology*, 110:365-367.

Ogawa, et al. 2005. Effects of R-102444 and its active metabolite R-96544, selective 5-HT$_{2A}$ receptor antagonists, on experimental acute and chronic pancreatitis: Additional evidence for possible involvement of 5-HT$_{2A}$ receptors in the development of experimental pancreatitis. *European Journal of Pharmacology*, 521:156-163.

Oláh, et al. 1956. Notiz über die N-formylierung von aminen mit formylfluorid. *Chem. Ber.*, 89:2211-2212.

Old, et al. 2002. Efficient palladium-catalyzed N-arylation of indoles. *Organic Letters*, 2(10):1403-1406.

Pace, et al. 1991. A mutant α subunit of G$_{12}$ induces neoplastic transformation of Rat-1 cells. *Proc. Natl. Acad. Sci. USA*, vol. 88:7031-7035.

Paiva, et al. 1988. Effects of ritanserin on sleep disturbances of dysthymic patients. *Psychopharmacology*, 96:395-399.

Patel, et al. 2004. The highly selective 5-hydroxytryptamine (5-HT)$_{2A}$ receptor antagonist, EMD 281014, significantly increases swimming and decreases immobility in male congenital learned helpless rats in the forced swim test. *Synapse*, 52:73-75.

Pierce, et al. 1995. 5-hydroxytryptamine-induced synovial plasma extravasation is mediated via 5-hydroxytryptamine2A receptors on sympathetic efferent terminals *The Journal of Pharmacology and Experimental Therapeutics*, 275(1):502-508.

Pollak, et al. 1999. Clozapine in drug-induced psychosis in Parkinson's disease. *The Lancet*, 353:2041-2042.

Read, W. T. 1922. Researches on hydantoins. Synthesis of the soporific, 4,4-phenylethyl-hydantoin(nirvanol). *J. Am. Chem. Soc.*, 44:1746-1755.

Ricci, A. 2000. *Modern Animation Methods*. New York: Wiley-VCH.

Rice, et al. 1955. Raney nickel catalyzed N-alkylation of aniline and benzidine with alcohols. *J. Am. Chem, Soc.*, 77:4052-4054.

Rubiralta, M., Giralt, E., & Diez, A. 1991. *Studies in Organic Chemistry 43. Piperidine: Structure, Preparation, Reactivity and Synthetic Applications of Piperidine and its Derivatives*. New York: Elsevier.

Sadzot, et al. 1989. Hallucinogenic drug interactions at human brain 5-HT$_2$ receptors: Implications for treating LSD-induced hallucinogenesis. *Psychopharmacology*, 98:495-499.

Saltzman, et al. 1991. Cloning of the human serotonin 5-HT2 and 5-HT1C receptor subtypes. *Biochemical and Biophysical Research Communications*, 181(3):1469-1478.

Saxena, et al. 1990. Cardiovascular effects of serotonin agonists and antagonists. *Journal of Cardiovascular Pharmacology*, 15(Supp. 7):S17-S34.

Scheibye, et al. 1978. Studies on organophosphorus compounds XXI. The dimer of *p*-methoxyphenylthionophosphine sulfide as thiation reagent. A new route to thiocarboxamides. *Bull. Soc. Chim. Belg.*, 87:229-238.

Schins, et al. 2003. Increased coronary events in depressed cardiovascular patients: 5-$HT_{2A}$ receptor as missing link? *Psychosomatic Medicine*, 65:729-737.

Screttas, et al. 1978. Hydrolithiation of α-olefins by a regiospecific two-step process. Transformation of alkyl phenyl sulfides to alkyllithium reagents. *J. Org. Chem.*, 43(6):1064-1071.

Sharpley, et al. 1994. Slow wave sleep in humans: Role of 5-$HT_{2A}$ and 5-$HT_{2C}$ receptors. *Neuropharmacology*, 33(3/4):467-471.

Stefancich, et al. 1984. Agenti antiinflammatori non-steroidei: Nota III—sintesi ed attività analgesica-antiinfiammatoria di 4-(pirrol-1-il)-fenilacetamidi e di 4-(pirrol-1-il)fenetilamine. *Farmaco Ed. Sci.*, 39(9):752-764.

Stryjer, et al. 2003. Treatment of neuroleptic-induced akathisia with the 5-$HT_{2A}$ antagonist trazodone. *Clinical Neuropharmacology*, 26(3):137-141.

Tolstikov et al.1991 "Synthesis and Reactivity of N-substituted aminoamides, antiarrhythmic and local anaesthetic activity" *Russian Chemical Reviews* 60(4):420434.

Tsukamoto, et al. 1995. Synthesis and structure-activity studies of a series of 1-oxa-2,8-diazaspiro[4.5]decan-3-ones and related compounds as $M_1$ muscarinic agonists. *Chem. Pharm. Bull.*, 43(9):1523-1529.

Vallar, et al. 1987, Altered $G_s$ and adenylate cyclase activity in human GH-secreting pituitary adenomas. *Nature*, 330:566-568.

Van Laar, et al. 2001. Subchronic effects of the GABA-agonist lorazepam and the 5-$HT_{2A/2C}$ antagonist ritanserin on driving performance, slow wave sleep and daytime sleepiness in healthy volunteers. *Psychopharmacology*, 154:189-197.

Varma, et al. 1999. Microwave-accelerated solvent-free synthesis of thioketones, thiolactones, thioamides, thionoesters, and thioflavonoids. *Organic Letters*, 1(5):697-700.

Viola, et al. 2002. Ritanserin, a serotonin-2 receptor antagonist, improves ultradian sleep rhythmicity in young poor sleepers. *Clinical Neurophysiology*, 113:429-434.

Vogel, A. I. 1948. Physical properties and chemical constitution. Part XIX. Five-membered and six-membered carbon rings. *J. Chem. Soc.*, pp. 1809-1813.

Vogl, et al. 2002. Palladium-catalyzed monoarylation of nitroalkanes. *J. Org. Chem*, 67(1)106-111.

Weiner, et al. 2001. 5-Hydroxytryptamine$_{2A}$ receptor inverse agonists as antipsychotics. *The Journal of Pharmacology and Experimental Therapeutics*, 299(1):268-276.

Whitmore, et al. 1942. Abnormal Grignard reactions. XII. Sterically hindered aliphatic carbonyl compounds. II. Ketones containing the dineopentylcarbinyl group. *J. Am. Chem. Soc.*, 64:1247-1251.

Whitmore, et al. 1947. Higher hydrocarbons. IV. Six phenyleicosanes and six cyclohexyleicosanes. *J. Am. Chem. Soc.*, 69:235-237.

Wolf, V. V. 1952. Über alkin-amine I. Aryl-propargyl-amine. *Liebigs Ann. Chem.*, 576:35-45.

Wolfe, et al. 1996. An improved catalyst system for aromatic carbon-nitrogen bond formation: The possible involvement of bis(phosphine) palladium complexes as key intermediates. *J. Am. Chem. Soc.*, 118:7215-7216.

Yamada, et al. 1998. Alternative synthesis of TTF donors with a dioxolane ring, and synthesis of their dithiolane and oxathiolane analogues. *Tetrahedron Letters*, 39:7709-7712.

Yang, et al. 1999. Palladium-catalyzed amination of aryl halides and sulfonates. *Journal of Organometallic Chemistry*, 576:125-146.

Yasuhara, et al. 2000. An activated phosphate for an efficient amide and peptide coupling reagent. *J. Chem. Soc., Perkin Trans.* 1, 17:2901-2902.

Yin, et al. 2002. Pd-catalyzed intermolecular amidation of aryl halides: The discovery that xantphos can be trans-chelating in a palladium complex. *J. Am. Chem. Soc.*, 124:6043-6048.

International Preliminary Report on Patentability dated Mar. 27, 2007, for PCT/US2005/034813.

International Preliminary Report on Patentability dated Mar. 27, 2007, for PCT/US2005/034376.

Office Action dated Apr. 6, 2007, from U.S. Appl. No. 11/418,322, filed May 3, 2006.

Office Action dated May 8, 2007, from U.S. Appl. No. 11/417,866, filed May 3, 2006.

Notice of Allowability dated Mar. 5, 2007, from U.S. Appl. No. 10/601,070, filed Jun. 20, 2003.

Notice of Allowability dated Jun. 19, 2007, from U.S. Appl. No. 11/418,322, filed May 3, 2006.

Office Action dated Jun. 2, 2008, from U.S. Appl. No. 11/687,552, filed Mar. 16, 2007.

Office Action dated Jul. 17, 2008, from U.S. Appl. No. 10/802,970, filed Mar. 16, 2004.

Notice of Allowance and Fee(s) Due and Notice of Allowability dated Jul. 23, 2008, from U.S. Appl. No. 11/299,566, filed Dec. 12, 2005.

Dorwald, F.Z., "Side Reactions in Organic Synthesis: A Guide to Successful Synthesis Design" 2005 Wiley-VCH GmbH & KGaA, Wienheim.

March, et al., Journal of Advanced Organic Chemistry: Reactions, Mechanism and Structure, 5th Edition, p. 423.

* cited by examiner

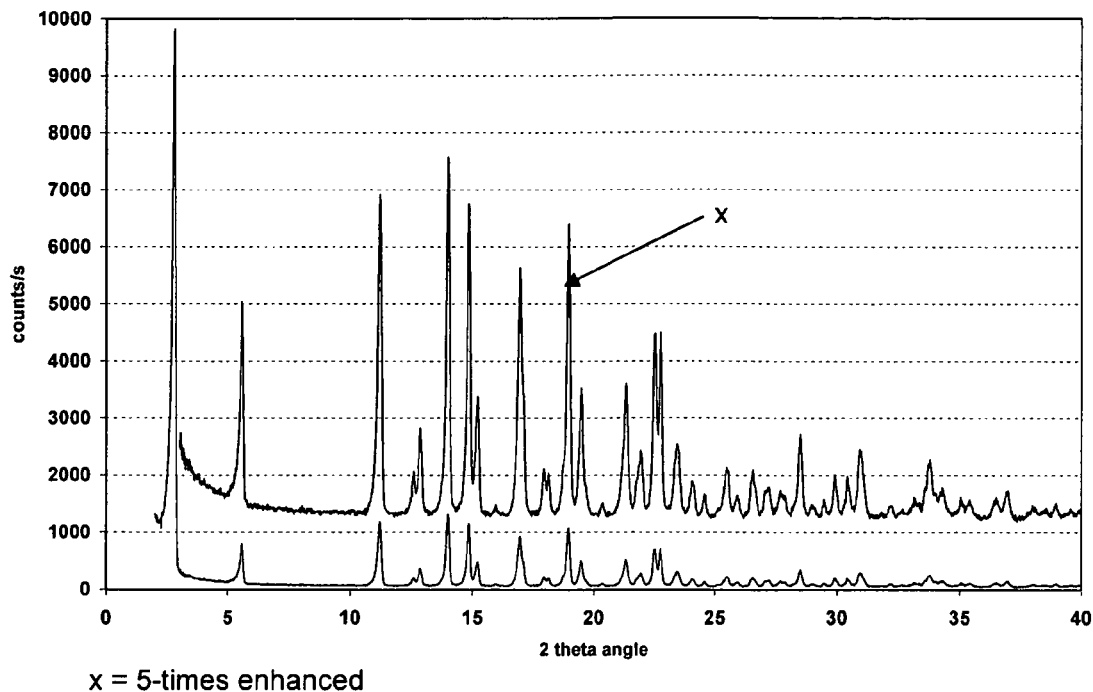
Figure 1: Crystalline citrate
x = 5-times enhanced
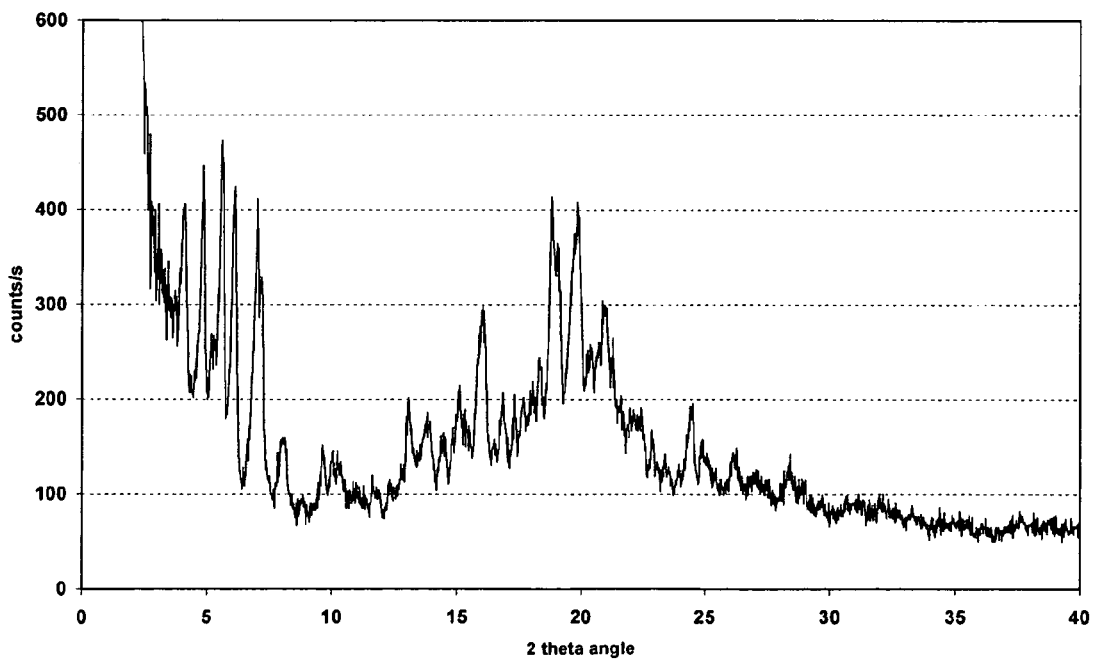
Figure 2: Crystalline fumarate form A

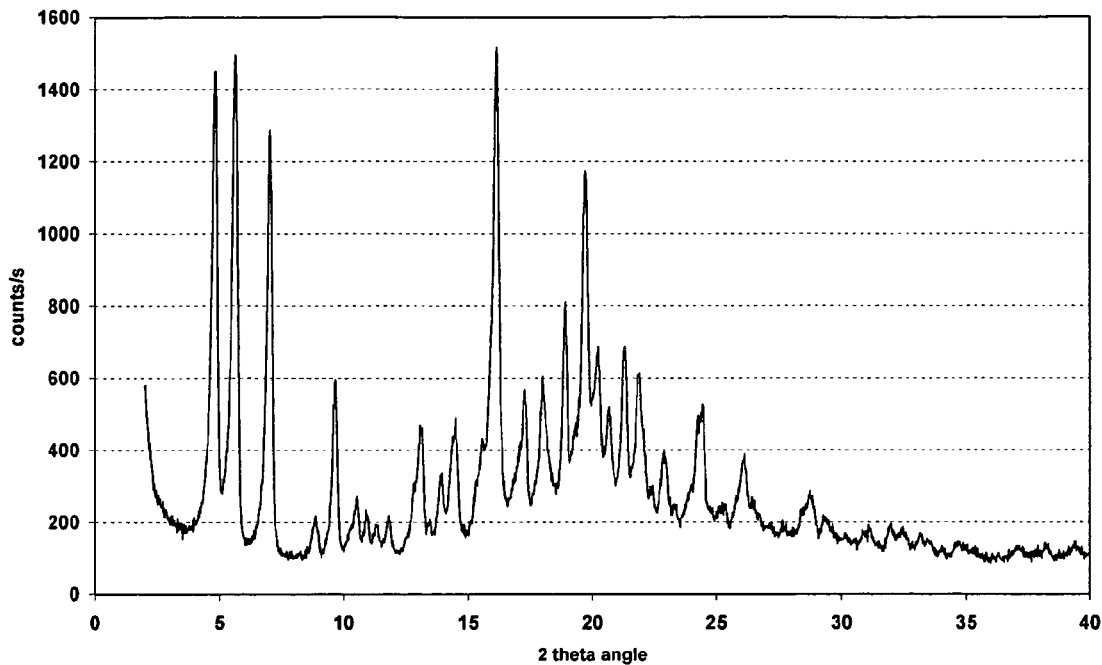
Figure 3: Crystalline fumarate form B
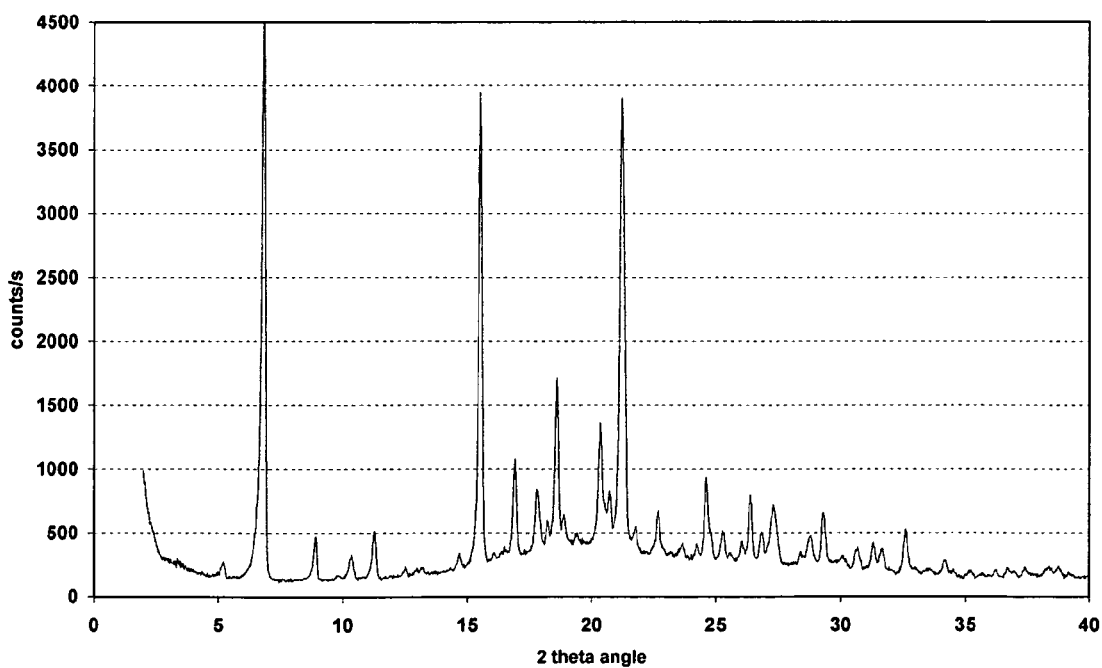
Figure 4: Crystalline maleate

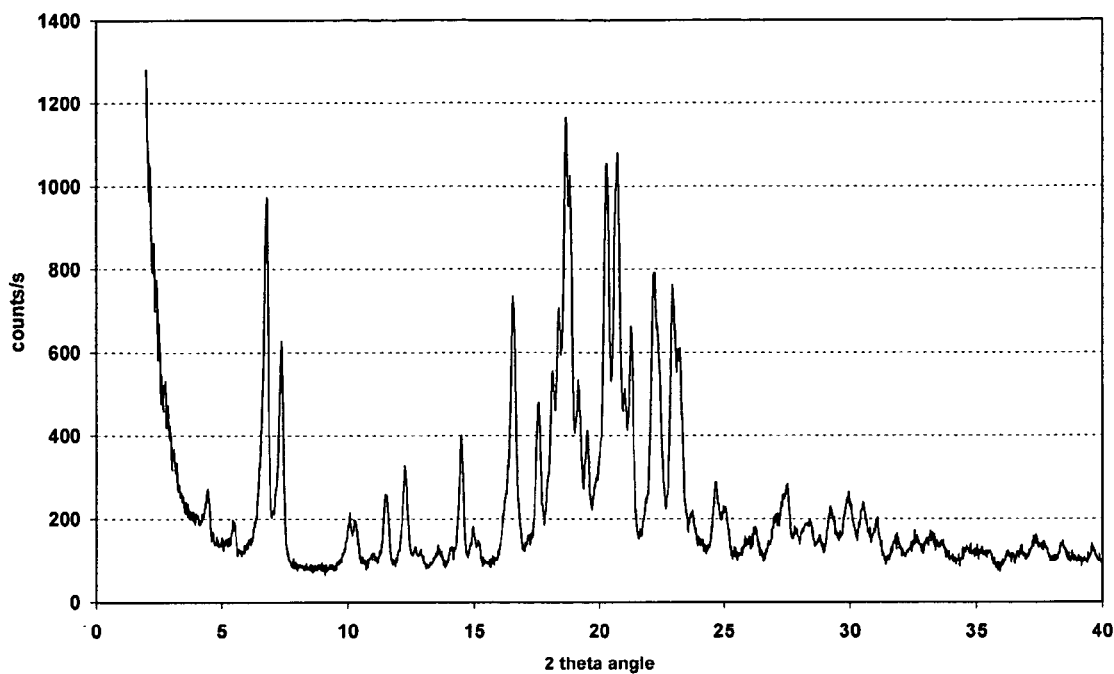
Figure 5: Crystalline malate
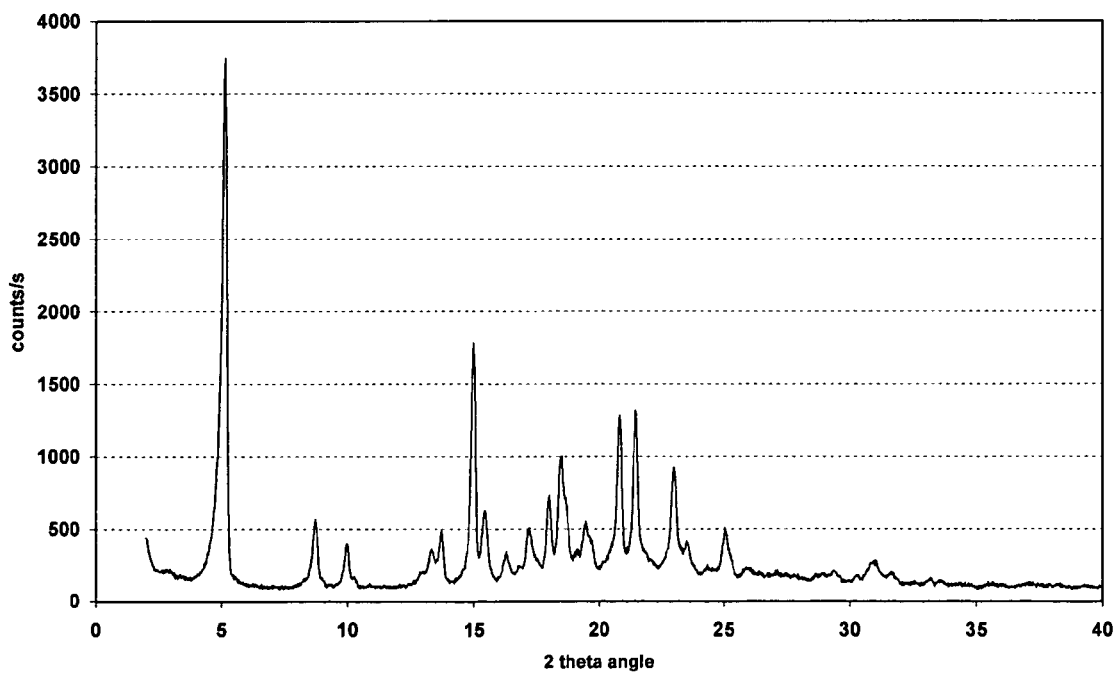
Figure 6: Crystalline phosphate

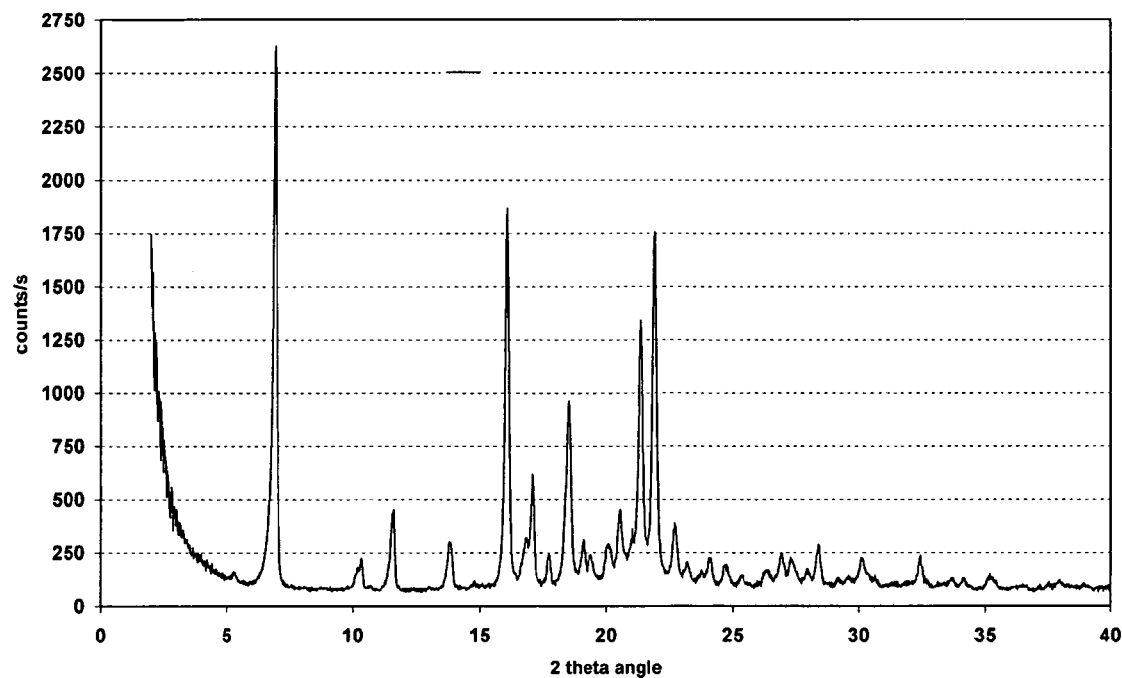
Figure 7: Crystalline succinate
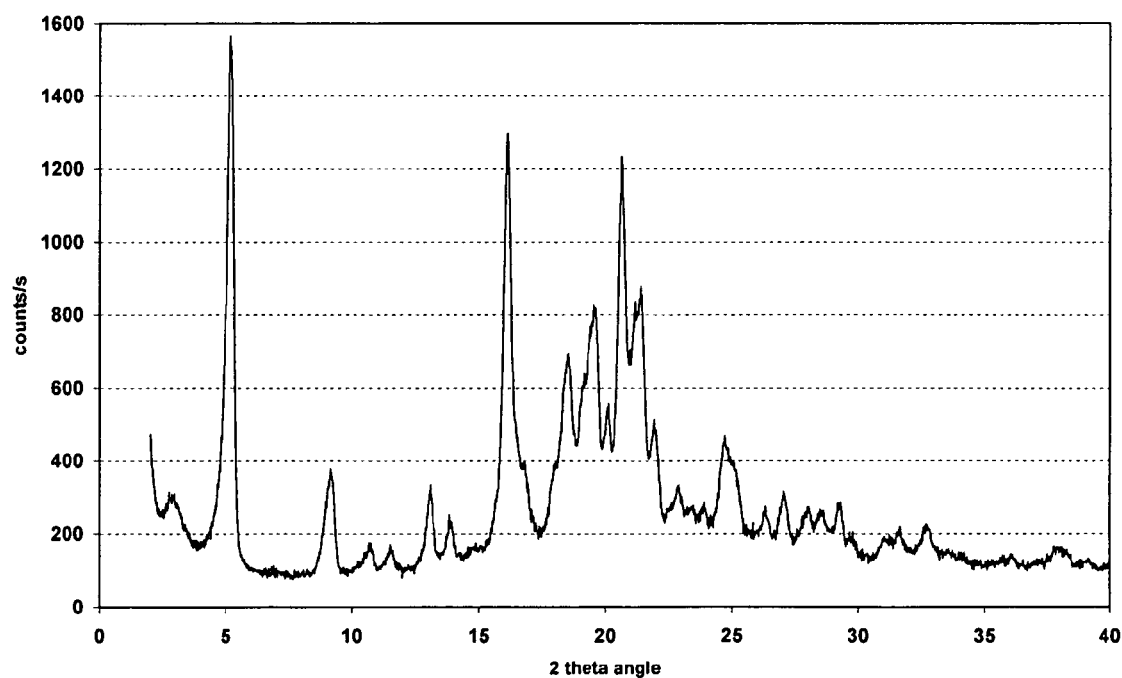
Figure 8: Crystalline sulphate

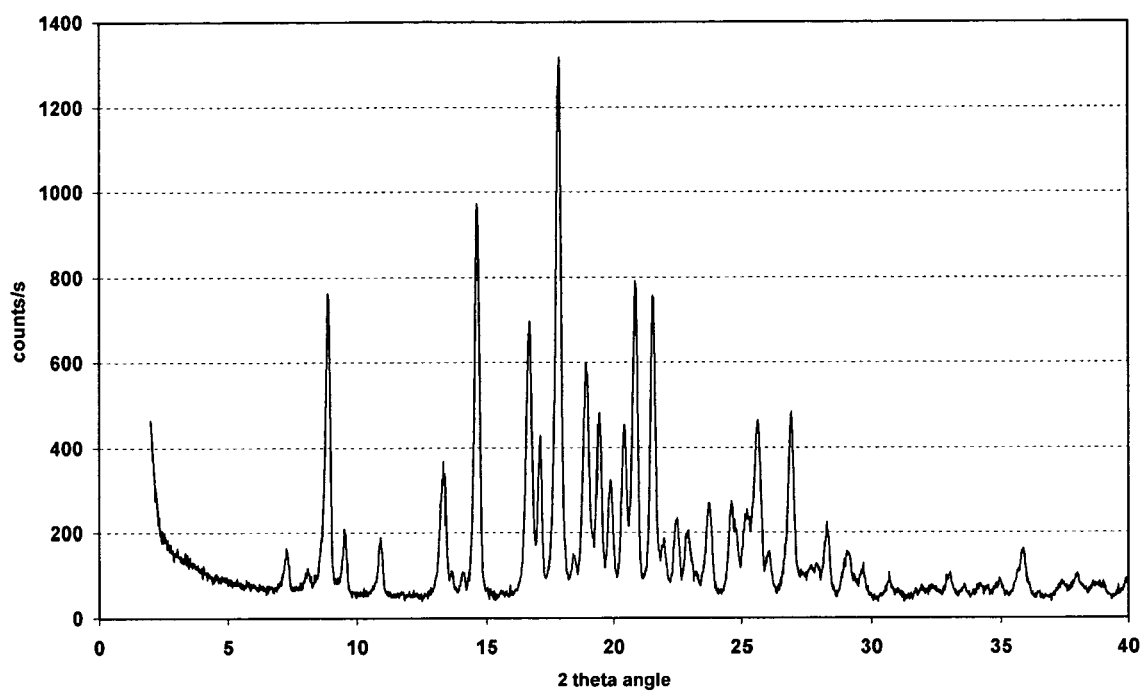
Figure 9: Crystalline edisylate

SALTS OF N-(4-FLUOROBENZYL)-N-(1-METHYL PIPERIDIN-4-Y1)-N'-(4-(2-METHYL PROPYLOXY)PHENYLMETHYL)CARBAMIDE AND THEIR PREPARATION

CROSS-REFERENCE TO RELATED APPLICATIONS

This application is a non-provisional of U.S. Provisional Application No. 60/614,014, filed on Sep. 27, 2004, entitled "SYNTHESIS OF 1-(4-FLUOROBENZYL)-3-(4-ISOBUTOXYBENZYL)-1-(1-METHYLPIPERIDIN-4-YL) UREA, ITS SALTS, AND POLYMORPHS," which is incorporated herein by reference in its entirety.

BACKGROUND OF THE INVENTION

1. Field of the Invention

The present invention relates to the fields of medicine and chemistry. More particularly, the present invention relates to N-(4-fluorobenzyl)-N-(1-methylpiperidin-4-yl)-N'-(4-(2-methylpropyloxy)-phenylmethyl)carbamide, its salts, and syntheses and uses thereof.

2. Description of the Related Art

WO 01/66521 describes N-azacycloalkyl-N-aralkyl carbamides and carboxylic acid amides, which constitute a new class of compounds effective in inhibiting an activity of monoamine receptors, including the serotonin receptor of the 5-HT2A subclass. WO 01/66521 is incorporated herein by reference in its entirety. Examples of disease conditions for which such compounds can be used include, but are not limited to, neuropsychiatric diseases such as schizophrenia and related idiopathic psychoses, depression, anxiety, sleep disorders, appetite disorders, affective disorders such as major depressions, bipolar disorder, depression with psychotic features and Tourette's Syndrome. Other beneficial treatments may be drug-induced psychoses and side-effects of Parkinson's disease as well as psychoses secondary to neurodegenerative disorders such as Alzheimer's or Huntington's Disease, hypertension, migraine, vasospasm, ischemia and the primary treatment and secondary prevention of various thrombotic conditions including myocardial infarction, thrombotic or ischemic stroke, idiopathic and thrombotic thrombocytopenic purpura and peripheral vascular disease.

SUMMARY OF THE INVENTION

One embodiment disclosed herein includes a salt of N-(4-fluorobenzyl)-N-(1-methylpiperidin-4-yl)-N'-(4-(2-methylpropyloxy)phenylmethyl)carbamide of formula I,

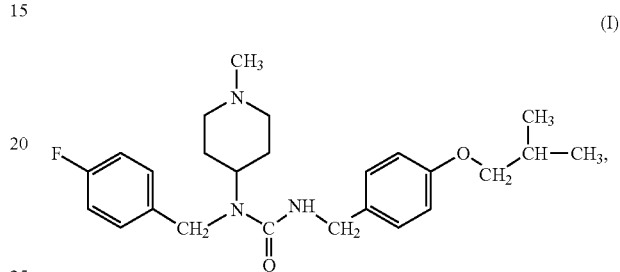

(I)

that includes an anion selected from the group consisting of phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, and naphthalenesulfonate. In some embodiments, the anion is selected from the group consisting of citrate, fumarate, maleate, malate, phosphate, succinate, sulphate, and edisylate. In one embodiment, when the anion is selected from the group consisting of citrate, maleate, malate, phosphate, succinate, and sulphate, the stoichiometry is 1:1 and when the anion is selected from the group consisting of edisylate and fumarate, the stoichiometry is 2:1. In one embodiment, the salt is a citrate of formula IV,

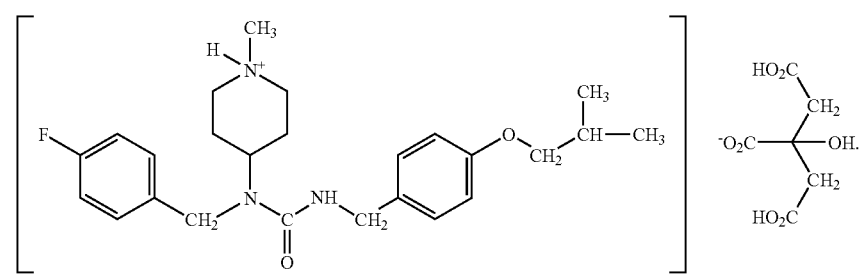

(IV)

One embodiment of the citrate salt exhibits a X-ray powder diffraction pattern comprising peaks having d-values in angstroms of about 31.8, about 15.9, about 7.9, about 6.3, about 5.96, about 5.23, and about 4.68.

In another embodiment, the salt is a fumarate of formula V,

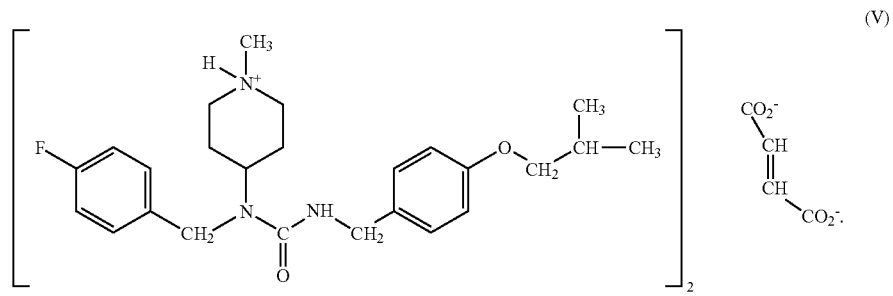

In one embodiment, the fumarate salt exhibits a X-ray powder diffraction pattern comprising peaks having d-values in angstroms of about 21.7, about 18.3, about 15.7, about 14.5, about 12.6, about 12.3, about 10.9, about 5.52, about 4.72, and about 4.47. In another embodiment, the fumarate salt exhibits a X-ray powder diffraction pattern comprising peaks having d-values in angstroms of about 18.4, about 15.7, about 12.6, about 9.2, about 5.50, about 4.93, about 4.70, about 4.51, about 4.17, and about 4.06.

In one embodiment, the salt is a maleate of formula VI,

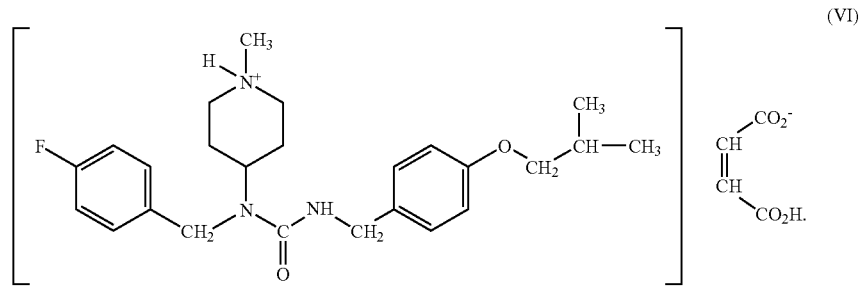

In one embodiment, the maleate salt exhibits a X-ray powder diffraction pattern comprising peaks having d-values in angstroms of about 13.0, about 5.71, about 5.24, about 4.77, about 4.37, and about 4.19.

In another embodiment, the salt is a malate of formula VII,

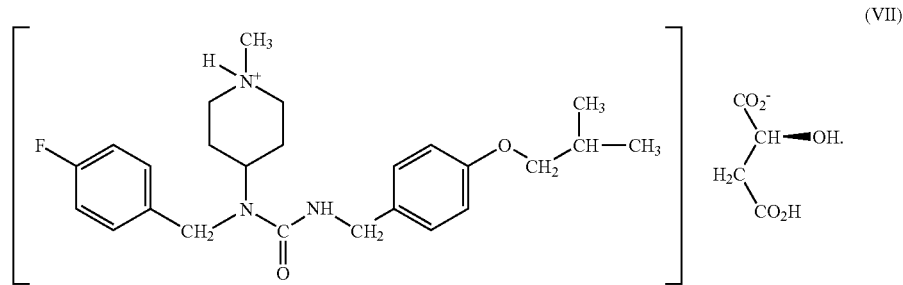

In one embodiment, the malate salt exhibits a X-ray powder diffraction pattern comprising peaks having d-values in angstroms of about 13.1, about 12.0, about 5.35, about 5.05, about 4.83, about 4.75, about 4.71, about 4.37, about 4.29, about 4.17, about 4.00, about 3.87, and about 3.83.

In another embodiment, the salt is a phosphate of formula VIII,

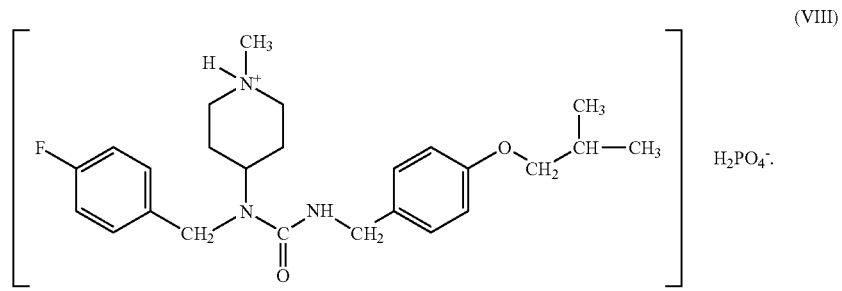

(VIII)

In one embodiment, the phosphate salt exhibits a X-ray powder diffraction pattern comprising peaks having d-values in angstroms of about 17.3, about 5.91, about 4.80, about 4.27, about 4.14, and about 3.86.

In another embodiment, the salt is a succinate of formula IX,

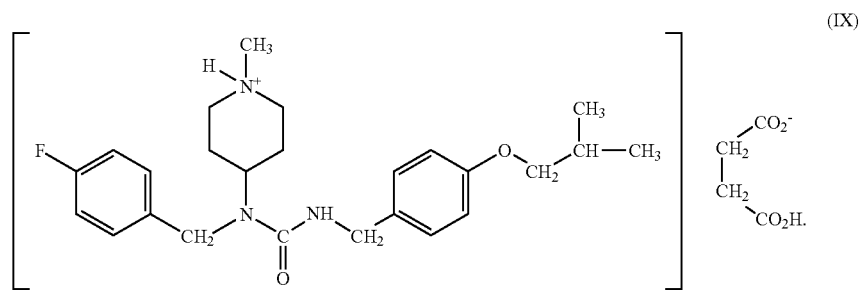

(IX)

In one embodiment, the succinate salt exhibits a X-ray powder diffraction pattern comprising peaks having d-values in angstroms of about 12.8, about 7.6, about 5.51, about 5.19, about 4.79, about 4.16, and about 4.05.

In another embodiment, the salt is a sulphate of formula X,

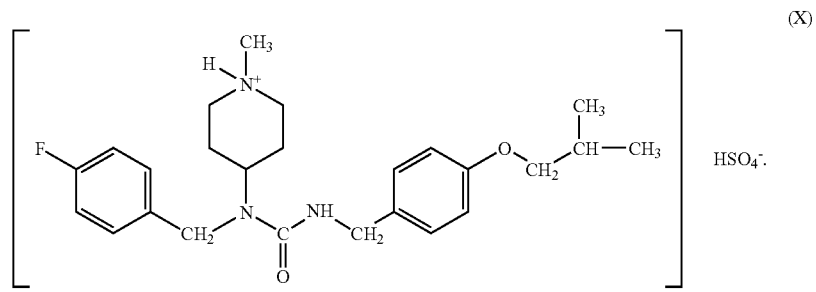

(X)

In one embodiment, the sulphate salt exhibits a X-ray powder diffraction pattern comprising peaks having d-values in angstroms of about 17.0, about 9.6, about 5.49, about 4.79, about 4.65, about 4.53, about 4.30, about 4.15, about 4.04, and about 3.89.

In another embodiment, the salt is an edisylate (ethanedisulfonate) of formula XI,

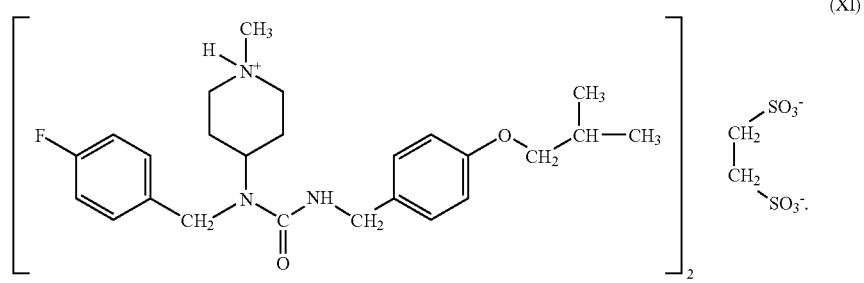

(XI)

In one embodiment, the edisylate salt exhibits a X-ray powder diffraction pattern comprising peaks having d-values in angstroms of about 10.0, about 6.05, about 5.31, about 4.97, about 4.68, about 4.26, and about 4.12.

Another embodiment disclosed herein includes a process for the preparation of a salt disclosed above, including:
a) forming a solution of the compound of formula I in an organic solvent;
b) adding an acid selected from the group consisting of citric acid, fumaric acid, maleic acid, L-(–)-malic acid, phosphoric acid, succinic acid, sulphuric acid, or 1,2-ethane disulfonic acid to said solution; and
c) isolating the salt.

In one embodiment, the isolating includes separating the salt from a suspension formed after step b). In another embodiment, the isolating includes precipitating the salt from a solution formed after step b) by one or more of cooling, solvent removal, or adding a non-solvent.

Another embodiment disclosed herein includes a salt of N-(4-fluorobenzyl)-N-(1-methylpiperidin-4-yl)-N'-(4-(2-methylpropyloxy)phenylmethyl) carbamide of formula I,

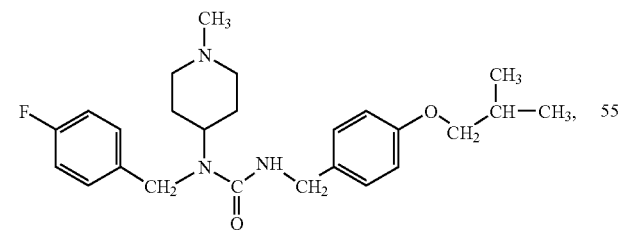

(I)

produced by a process comprising:
a) forming a solution of the compound of formula I in an organic solvent;
b) adding an acid selected from the group consisting of citric acid, fumaric acid, maleic acid, L-(–)-malic acid, phosphoric acid, succinic acid, sulphuric acid, or 1,2-ethane disulfonic acid to said solution; and
c) isolating the salt.

Another embodiment disclosed herein includes a pharmaceutical composition comprising a salt of N-(4-fluorobenzyl)-N-(1-methylpiperidin-4-yl)-N'-(4-(2-methylpropyloxy)phenylmethyl)carbamide of formula I,

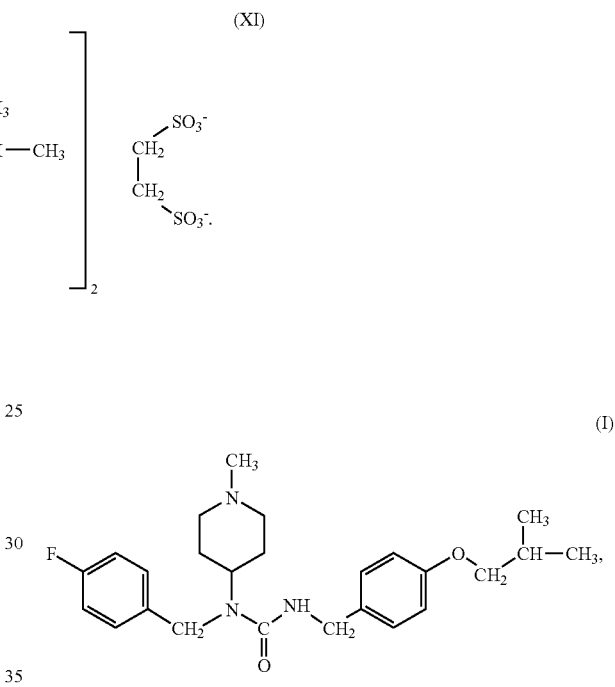

(I)

that includes an anion selected from the group consisting of phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, and naphthalenesulfonate and a pharmaceutically acceptable carrier.

Another embodiment disclosed herein includes a method for the treatment of a neuropsychiatric disease, comprising administering to a subject at least one salt of N-(4-fluorobenzyl)-N-(1-methylpiperidin-4-yl)-N'-(4-(2-methylpropyloxy)phenylmethyl)carbamide of formula I,

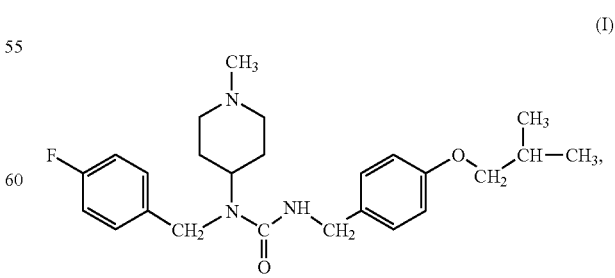

(I)

wherein the salt comprises an anion selected from the group consisting of phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, and naphthalenesulfonate. In one embodiment, the neuropsychiatric disease is selected from the group consisting of psychosis, schizophrenia, schizoaffective disorders, mania, psychotic depression, affective disorders, dementia, anxiety, sleep disorders, appetite disorders, bipolar disorder, psychosis secondary to hypertension, migraine, vasospasm, and ischemia, motor tics, tremor, psychomotor slowing, bradykinesia, and neuropathic pain.

Another embodiment disclosed herein includes a method of inhibiting an activity of a monoamine receptor, comprising administering to a subject at least one salt as described above.

Another embodiment disclosed herein includes a method for the treatment of neurodegenerative diseases, comprising administering to a subject at least one salt as described above. In some embodiments, the neurodegenerative disease is selected from the group consisting Parkinson's disease, Huntington's disease, Alzheimer's disease, Spinocerebellar Atrophy, Tourette's Syndrome, Friedrich's Ataxia, Machado-Joseph's disease, Lewy Body Dementia, Dystonia, Progressive Supranuclear Palsy, and Frontotemporal Dementia.

Another embodiment disclosed herein includes a method for treating dyskinesia associated with dopaminergic therapy, comprising administering to a subject at least one salt as described above.

Another embodiment disclosed herein includes a method for treating dystonia, myoclonus, or tremor associated with dopaminergic therapy, comprising administering to a subject at least one salt as described above.

Another embodiment disclosed herein includes a method for treating a thrombotic condition, comprising administering to a subject at least one salt as described above. In some embodiments, the thrombotic condition is selected from the group consisting of myocardial infarction, thrombotic or ischemic stroke, idiopathic and thrombotic thrombocytopenic purpura, peripheral vascular disease, and Raynaud's disease.

BRIEF DESCRIPTION OF THE DRAWINGS

FIG. 1 is a X-ray powder diffraction pattern of the crystalline citrate salt of the compound of formula IV.

FIG. 2 is a X-ray powder diffraction pattern of form A of the crystalline fumarate salt of the compound of formula V.

FIG. 3 is a X-ray powder diffraction pattern of form B of the crystalline fumarate salt of the compound of formula V.

FIG. 4 is a X-ray powder diffraction pattern of the crystalline maleate salt of the compound of formula VI.

FIG. 5 is a X-ray powder diffraction pattern of the crystalline malate salt of the compound of formula VII.

FIG. 6 is a X-ray powder diffraction pattern of the crystalline phosphate salt of the compound of formula VIII.

FIG. 7 is a X-ray powder diffraction pattern of the crystalline succinate salt of the compound of formula IX.

FIG. 8 is a X-ray powder diffraction pattern of the crystalline sulphate salt of the compound of formula X.

FIG. 9 is a X-ray powder diffraction pattern of the crystalline edisylate salt of the compound of formula XI.

DETAILED DESCRIPTION OF THE PREFERRED EMBODIMENT

One useful N-azacycloalkyl-N-aralkyl carbamide is N-(4-fluorobenzyl)-N-(1-methylpiperidin-4-yl)-N'-(4-(2-methylpropyloxy)phenylmethyl)carbamide of formula I:

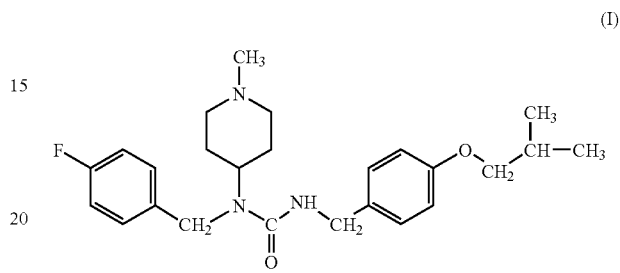

(I)

Synthesis of N-(4-fluorobenzyl)-N-(1-methylpiperidin-4-yl)-N'-(4-(2-methylpropyloxy) phenylmethyl)carbamide One embodiment is a method of synthesizing the compound of formula (I) comprises reacting the compound of formula II ((4-fluorobenzyl)-(1-methylpiperidin-4-yl)amine)

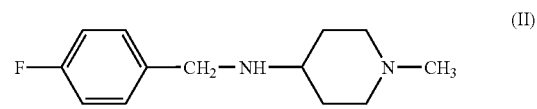

(II)

with the compound of formula III (4-(2-methylpropyloxy) phenylmethyl-isocyanate)

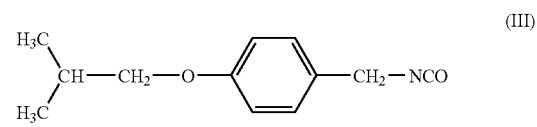

(III)

In one embodiment, about 0.9 to about 1.1 equivalents of (4-fluorobenzyl)-(1-methylpiperidin-4-yl)amine per equivalent of 4-(2-methylpropyloxy)phenylmethyl-isocyanate is used. In some embodiments, the resulting compound of formula I is isolated from the reaction mixture. In one embodiment, a salt-forming acid is added after the reaction. The formed salt may be isolated by solvent removal, precipitation, or both solvent removal and precipitation, followed by deliberation of the compound of formula I under alkaline aqueous conditions through dissolution in an organic solvent in a two phase system, and separating the compound of formula I from the organic solution. In a preferred embodiment, 1.0 equivalent of (4-fluorobenzyl)-(1-methylpiperidin-4-yl)amine per equivalent of 4-(2-methylpropyloxy)phenylmethyl-isocyanate is used in the reaction. The reaction may be carried out in the presence of Lewis acids as catalysts such as metal salts or more preferably metal alkoxylates. Some examples are $MgCl_2$, $FeCl_2$, $FeCl_3$, $FeBr_2$, $Fe(SO_4)_2$, $NiCl_2$, $BCl_3$, $AlCl_3$, $BBr_3$, $TiCl_4$, $TiBr_4$, $ZrCl_4$, $BCl_3$, $Al(O-C_1-C_4-Alkyl)_3$, and $Ti(O-C_1-C_4-Alkyl)_3$. The amount of catalyst may be from about 0.0001 to about 5 percent by weight and preferably about 0.01 to about 3 percent by weight relative to the compound of formula II.

The reaction is preferably carried out in the presence of an inert organic solvent such as aliphatic ethers (e.g., diethyl ether, methyl propyl ether, dibutyl ether, ethylene glycol dimethyl ether, tetrahydrofuran or dioxane), esters of aliphatic carboxylic acids or alcohols (e.g., $C_2$-$C_4$ alkyl esters of acetic acid), lactones (e.g., valerolactone), halogenated hydrocarbons (e.g., di- or trichloromethane, tetrachloroethane), or aliphatic $C_3$-$C_8$ ketones (e.g., acetone, methyl propyl ketone, diethyl ketone, or methyl i- or t-butyl ketone).

The reaction temperature is preferably in the range of about −30° C. to about 60° C. and more preferably in the range of about 5° C. to about 30° C. The reaction time may be controlled by monitoring the consumption of the compound of formula II or formula III either by on-line process analytics, or by recovering and analyzing samples offline.

Isolation of the compound of formula I may be performed by any suitable method including removal of the solvent by distillation of the reaction residue under reduced pressure and lower temperatures, such as up to about 100° C., preferably up to about 80° C. Isolation may also occur by partial removal of solvent to increase the concentration, filtering of impurities, precipitating the solid compound of formula I either by further concentration or addition of a non-solvent such as an aliphatic hydrocarbon (e.g., pentane, hexane, heptane, octane, cyclohexane, methylcyclohexane, or water), filtering of the solid, and drying. The isolated compound of formula I may be purified by known methods such as distillation or chromatographic methods.

It was found that removal of impurities such as formed side-products prior to the isolation is a convenient route to produce the compound of formula I with high purity. It was further found that purification can be effectively improved by forming salts of the carbamide, which can be precipitated as crystalline compounds and re-crystallized from solvents to remove impurities. The free carbamide of formula I is then deliberated by dissolution of the salt in water, addition of a base, and extraction of the carbamide with an organic solvent. The organic solutions may be washed with water and aqueous sodium chloride before removal of the solvent by distillation, optionally under reduced pressure. Impurities may be removed in this method by precipitation or dissolution in water in then use of a two phase systems. When precipitation of the salt is desired for easy isolation by filtration or centrifugation, partial removal of the organic solvent and addition of fresh solvent may be carried out. Suitable solvents with low salt solubility are aprotic organic solvents such as hydrocarbons, halogenated hydrocarbons, ethers, ketones, carboxylic acid esters and lactones, acetonitrile, and alcohols having at least 3 carbon atoms.

The starting materials for the above-described reaction can be obtained by known and analogous methods. Specifically, the compound of formula II may be obtained by the reaction of N-methylpiperid-4-one with 4-fluorobenzylamine in the presence of a metal hydride, for example according to the scheme

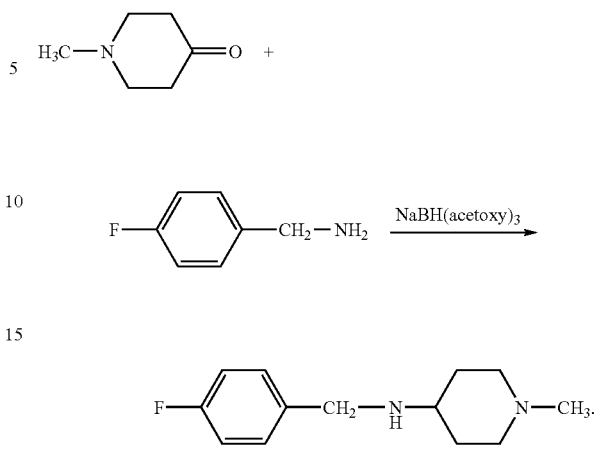

Compounds of formula III may be prepared by reacting 4-hydroxybenzaldehyde with isobutylhalogenide (e.g., isobutylbromogenide) to form 4-isobutoxybenzaldehyde, which may be converted with hydroxylamine to the aldoxime form:

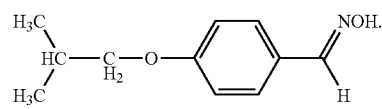

This oxime may be catalytically hydrogenated with a palladium catalyst to the corresponding 4-isobutoxybenzylamine, from which the isocyanate of formula III may be obtained by reaction with phosgene.

Salts of N-(4-fluorobenzyl)-N-(1-methylpiperidin-4-yl)-N'-(4-(2-methylpropyloxy) phenylmethyl)carbamide Some embodiments are salts of N-(4-fluorobenzyl)-N-(1-methylpiperidin-4-yl)-N'-(4-(2-methylpropyloxy)phenylmethyl)carbamide comprising an anion selected from the group consisting of phosphate, sulphate, nitrate, diphosphate, bicarbonate, carbonate, clavulanate, isothionate, borate, halide, nitrate, acetate, succinate, lactate, lactobionate, laurate, mandelate, malate, citrate, fumarate, maleate, oleate, oxalate, ascorbate, nicotinate, benzoate, mesylate, salicylate, stearate, tannate, tosylate, valerate, methanesulfonate, ethanesulfonate, benzenesulfonate, p-toluensulfonate, 2-ethane disulfonate, or naphthalenesulfonate.

The salts may be obtained as crystalline solids. When the anion is citrate, maleate, malate, phosphate, succinate, or sulphate, the salt has a 1:1 stoichiometry. The edisylate shows a 2:1 stoichiometry of the free base to the acid and the fumarate also presumably has a 2:1 stoichiometry. In some embodiments, the salts may form hydrates or other solvates. Specifically, it has been found that the malate and succinate can form hydrates. In some embodiments, various polymorphic forms of the salts are provided. In some embodiments, the salts are amorphous.

In one embodiment, the salt is the citrate of formula IV,

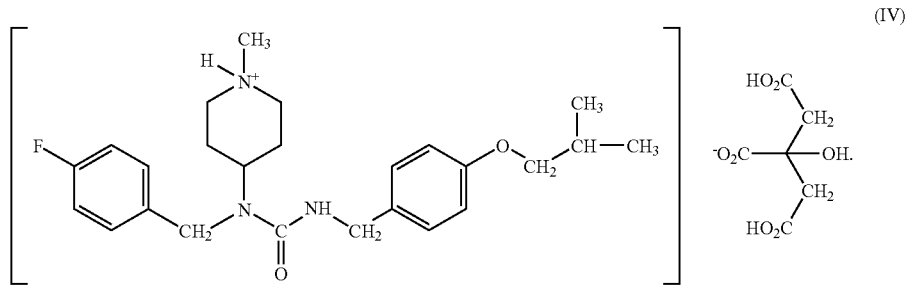

One embodiment provides a crystalline form of the citrate of formula IV, which exhibits the X-ray powder diffraction pattern depicted in FIG. 1; hereinafter designated as crystalline citrate. Specifically the X-ray powder diffraction pattern exhibits the following characteristic peaks expressed in d-values (Å): 31.8 (vs), 15.9 (m), 7.9 (m), 6.9 (w), 6.3 (m), 5.96 (m), 5.83 (w), 5.23 (m), 4.68 (m), 4.56 (m), 4.17 (m), 4.05 (w), 3.95 (m), 3.91 (m), 3.79 (w), 3.49 (w), and 3.13 (w). The abbreviations in parenthesis are used herein as follows: (vs)= very strong intensity, (s)=strong intensity, (m)=medium intensity, (w)=weak intensity, and (vw)=very weak intensity. In various embodiments, crystalline citrate is present in amounts of at least about 50%, 70%, 80%, 90%, 95%, or 98%, with the remainder being other salt or crystalline forms (including hydrates and solvates) and/or amorphous forms of the compound of formula I.

Another embodiment is the fumarate salt of formula V, being other salt or crystalline forms (including hydrates and solvates) and/or amorphous forms of the compound of formula I.

Crystalline fumarate form A can also exist in mixtures with the amorphous form and/or with crystalline fumarate form B. Crystalline fumarate form B exhibits the X-ray power diffraction pattern depicted in FIG. 3. Specifically the X-ray powder diffraction pattern exhibits the following characteristic peaks expressed in d-values (Å): 18.4 (vs), 15.7 (vs), 12.6 (vs), 10.0 (w), 9.2 (m), 6.8 (m), 6.37 (m), 6.12 (m), 5.68 (m), 5.50 (vs), 5.13 (m), 4.93 (s), 4.70 (s), 4.51 (s), 4.39 (m), 4.30 (m), 4.17 (s), 4.06 (s), 3.88 (m), 3.81 (w), 3.66 (m), 3.64 (m), 3.42 (m). In various embodiments, crystalline fumarate form B is present in amounts of at least about 50%, 70%, 80%, 90%, 95%, or 98%, with the remainder being other salt or crystalline forms (including hydrates and solvates) and/or amorphous forms of the compound of formula I.

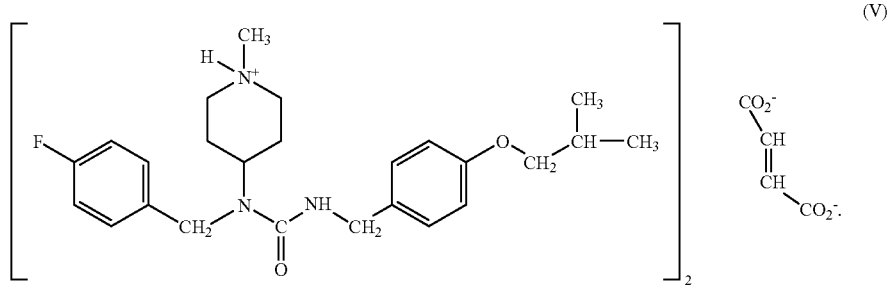

One embodiment provides a crystalline form of the fumarate of formula V, which exhibits the X-ray powder diffraction pattern depicted in FIG. 2; hereinafter referred to as crystalline fumarate form A. Specifically the X-ray powder diffraction pattern exhibits the following characteristic peaks expressed in d-values (Å): 21.7 (m), 18.3 (s), 15.7 (s), 14.5 (s), 12.6 (s), 12.3 (m), 10.9 (w), 9.1 (w), 6.8 (w), 6.40 (w), 5.87 (w), 5.52 (m), 5.26 (m), 5.12 (w), 4.72 (s), 4.66 (s), 4.51 (m), 4.47 (s), 4.24 (m), 3.64 (m). In various embodiments, crystalline fumarate form A is present in amounts of at least about 50%, 70%, 80%, 90%, 95%, or 98%, with the remainder Crystalline fumarate form A may be obtained from rapid crystallization procedures with cooling rates from about 10-100° C. per hour, more preferably about 30-60° C. per hour, and recovering the solid shortly after the suspension is cooled from about 60° C. to 23±2° C., or below. Crystalline fumarate form B may be obtained from slower crystallization procedures with cooling rates from 1-60° C. per hour, more preferably form 5-20° C. per hour, with subsequent stirring of the obtained suspension at temperatures from 5° C. to 40° C. for at least one, but up to 60 hours, more preferably for about 24 hours at 23±2° C.

Another embodiment is the maleate salt of formula VI,

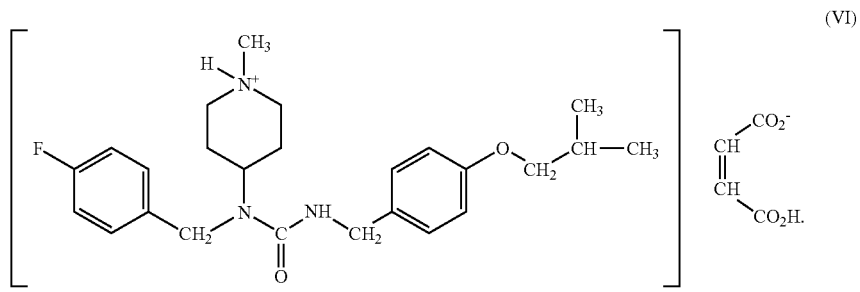

(VI)

One embodiment provides a crystalline form of the maleate of formula VI, which exhibits the X-ray powder diffraction pattern depicted in FIG. 4; hereinafter referred to as crystalline maleate. Specifically the X-ray powder diffraction pattern exhibits the following characteristic peaks expressed in d-values (Å): 17.1 (w), 13.0 (vs), 10.0 (w), 8.6 (w), 7.9 (w), 5.71 (vs), 5.24 (m), 4.98 (m), 4.86 (w), 4.77 (m), 4.70 (w), 4.37 (m), 4.29 (w), 4.19 (vs), 3.92 (w), 3.76 (w), 3.67 (w), 3.62 (m), 3.52 (w), 3.38 (m), 3.27 (m), 3.05 (m). In various embodiments, crystalline maleate is present in amounts of at least about 50%, 70%, 80%, 90%, 95%, or 98%, with the remainder being other salt or crystalline forms (including hydrates and solvates) and/or amorphous forms of the compound of formula I.

Another embodiment is the malate salt of formula VII,

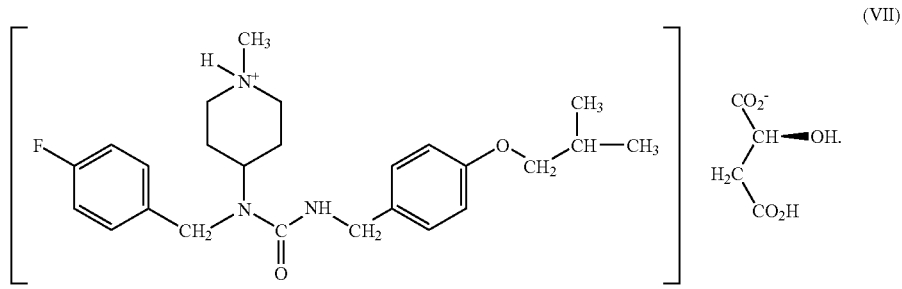

(VII)

One embodiment provides a crystalline form of the malate of formula VII, which exhibits the X-ray powder diffraction pattern depicted in FIG. 5; hereinafter referred to as crystalline malate. Specifically the X-ray powder diffraction pattern exhibits the following characteristic peaks expressed in d-values (Å): 19.8 (m), 16.2 (w), 13.1 (vs), 12.0 (s), 7.7 (m), 7.2 (m), 6.1 (m), 5.35 (s), 5.05 (s), 4.89 (m), 4.83 (s), 4.75 (vs), 4.71 (vs), 4.63 (m), 4.55 (m), 4.37 (vs), 4.29 (vs), 4.17 (s), 4.00 (s), 3.97 (m), 3.87 (s), 3.83 (s), 3.61 (m). Without being bound by any particular theory, this crystalline form of the malate of formula VII may be a sesquihydrate. In various embodiments, crystalline malate is present in amounts of at least about 50%, 70%, 80%, 90%, 95%, or 98%, with the remainder being other salt or crystalline forms (including hydrates and solvates) and/or amorphous forms of the compound of formula I.

Another embodiment is the phosphate salt of formula VIII,

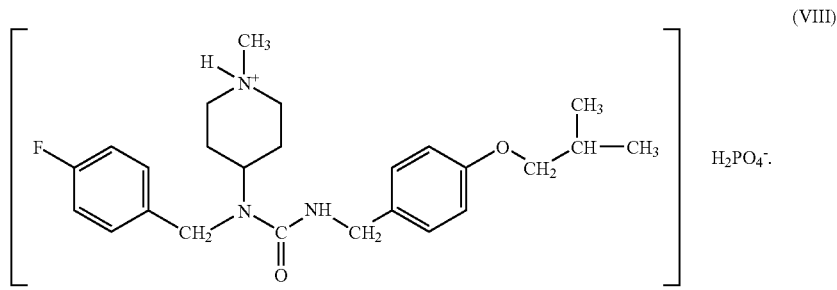

(VIII)

One embodiment provides a crystalline form of the phosphate of formula V, which exhibits the X-ray powder diffraction pattern depicted in FIG. 6; hereinafter referred to as crystalline phosphate. Specifically the X-ray powder diffraction pattern exhibits the following characteristic peaks expressed in d-values (Å): 17.3 (vs), 10.1 (m), 8.9 (m), 6.7 (w), 6.5 (m), 5.91 (s), 5.74 (m), 5.16 (w), 4.93 (m), 4.80 (m), 4.75 (w), 4.56 (m), 4.27 (m), 4.14 (m), 3.86 (m), 3.55 (m). In various embodiments, crystalline phosphate is present in amounts of at least about 50%, 70%, 80%, 90%, 95%, or 98%, with the remainder being other salt or crystalline forms (including hydrates and solvates) and/or amorphous forms of the compound of formula I.

Another embodiment is the succinate salt of formula IX,

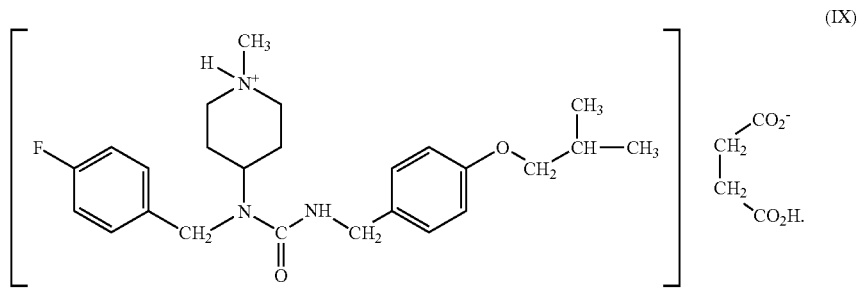

(IX)

One embodiment provides a crystalline form of the succinate of formula IX, which exhibits the X-ray powder diffraction pattern depicted in FIG. 7; hereinafter referred to as crystalline succinate. Specifically the X-ray powder diffraction pattern exhibits the following characteristic peaks expressed in d-values (Å): 12.8 (vs), 8.6 (w), 7.6 (m), 6.4 (w), 5.51 (s), 5.27 (w), 5.19 (m), 4.79 (m), 4.42 (w), 4.32 (m), 4.16 (s), 4.05 (s), 3.91 (m), 3.69 (w), 3.31 (w), 3.27 (w), 3.14 (w), 2.97 (w), 2.76 (w). In various embodiments, crystalline succinate is present in amounts of at least about 50%, 70%, 80%, 90%, 95%, or 98%, with the remainder being other salt or crystalline forms (including hydrates and solvates) and/or amorphous forms of the compound of formula I.

Another embodiment is the sulphate salt of formula X,

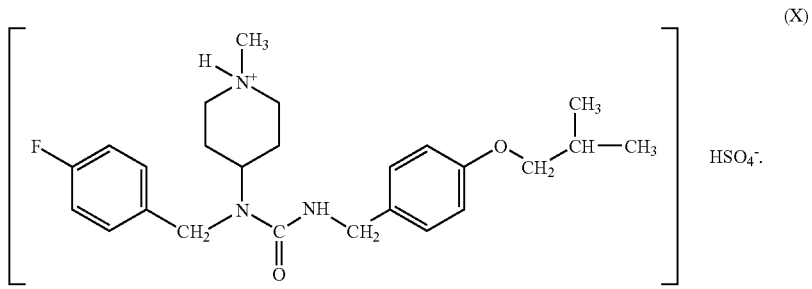

One embodiment provides a crystalline form of the sulphate of formula X, which exhibits the X-ray powder diffraction pattern depicted in FIG. 8; hereinafter referred to as crystalline sulphate. Specifically the X-ray powder diffraction pattern exhibits the following characteristic peaks expressed in d-values (Å): 17.0 (vs), 9.6 (m), 8.3 (w), 6.8 (m), 6.4 (m), 5.49 (vs), 5.29 (w), 4.79 (s), 4.65 (m), 4.53 (s), 4.42 (m), 4.30 (vs), 4.18 (m), 4.15 (s), 4.04 (m), 3.89 (w), 3.60 (m), 3.56 (w). In various embodiments, crystalline sulphate is present in amounts of at least about 50%, 70%, 80%, 90%, 95%, or 98%, with the remainder being other salt or crystalline forms (including hydrates and solvates) and/or amorphous forms of the compound of formula I.

Another embodiment is the edisylate (ethanedisulfonate) salt of formula XI,

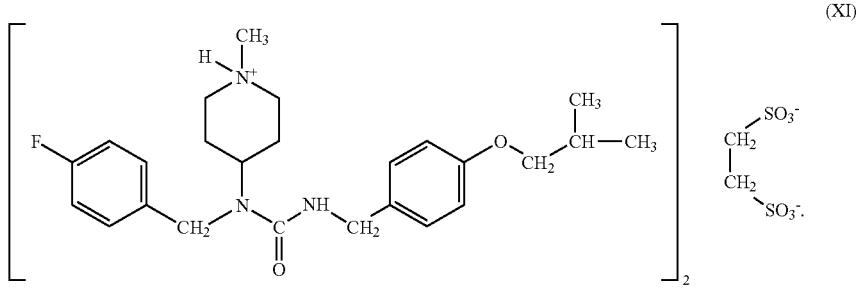

One embodiment provides a crystalline form of the edisylate of formula XI, which exhibits the X-ray powder diffraction pattern depicted in FIG. 9; hereinafter referred to as crystalline edisylate. Specifically the X-ray powder diffraction pattern exhibits the following characteristic peaks expressed in d-values (Å): 12.1 (m), 10.0 (s), 9.3 (m), 8.1 (m), 6.6 (m), 6.05 (vs), 5.31 (s), 5.18 (m), 4.97 (vs), 4.81 (w), 4.68 (s), 4.57 (m), 4.46 (m), 4.35 (m), 4.26 (s), 4.12 (s), 3.96 (m), 3.88 (w), 3.75 (m), 3.62 (m), 3.53 (w), 3.48 (m), 3.42 (w), 3.31 (m), 3.15 (w), 3.07 (w). In various embodiments, crystalline edisylate is present in amounts of at least about 50%, 70%, 80%, 90%, 95%, or 98%, with the remainder being other salt or crystalline forms (including hydrates and solvates) and/or amorphous forms of the compound of formula I.

Salts of the compound of formula I described herein may be prepared by the reaction of equivalent amounts of the base of formula I with an acid in a suitable inert organic solvent. Accordingly, one embodiment is a process for the preparation of a salt of N-(4-fluorobenzyl)-N-(1-methylpiperidin-4-yl)-N'-(4-(2methylpropyloxy)phenylmethyl)carbamide of formula I having anions selected from the group consisting of citrate, fumarate, maleate, malate, phosphate, succinate, sulphate and edisylate, that includes:
  a) forming a solution of the compound of formula I in an organic solvent;
  b) adding a suitable organic or inorganic acid to the solution; and
  c) isolating the salt of the compound of formula I from an obtained suspension, or precipitating the salt by cooling, solvent removal, adding a non-solvent, or a combination of these methods.

Suitable solvents include, but are not limited to, hydrocarbons such as toluene, halogenated hydrocarbons such as di- or trichloromethane, tetrachloroethane, esters of aliphatic carboxylic acids and alcohols ($C_2$-$C_4$alkyl esters of acetic acid) (ethyl acetate), lactones (valerolactone), acetonitrile, ethers (diethylether, methyl propyl ether, t-butyl-methyl-ether, dibutyl ether, ethylene glycol dimethyl ether, tetrahydrofuran or dioxane), aliphatic $C_3$-$C_8$ketones (acetone, methyl propyl ketone, diethyl ketone or methyl i- or t-butyl ketone), and alcohols (methanol, ethanol, n- or i-propanol and butanol).

Suitable salt-forming acids include but are not limited to phosphoric acid, sulphuric acid, nitric, diphosphate, bicarbonate, carbonic acid, clavulanic acid, isothionic acid, boric acid, hydrohalic acid (e.g., hydrochloric acid or hydrobromic acid), nitric acid, and aliphatic or aromatic carboxylic or sulfonic acids (e.g., acetic, succinic, lactic, lactobionic, lauric, mandelic, malic, tartaric, citric, fumaric, maleic, oleic, oxalic, ascorbic, nicotinic, benzoic, mesylic, salicylic, stearic, tannic, tosylic, valeric, methanesulfonic, ethanesulfonic, benzenesulfonic, p-toluensulfonic, salicylic, 2-ethane disulfonic, or naphthalenesulfonic acid).

When used, the non-solvent may be an aliphatic hydrocarbon such as petrol ether, pentane, hexane, heptane, octane, cyclopentane, cyclohexane or methylcyclohexane. Other non-solvents may be determined with solubility tests of a selected salt in various solvents.

Various crystallization techniques may be used to form and isolate crystalline compounds, such as stirring of a suspension (phase equilibration), precipitation, re-crystallization, solvent evaporation, cooling to initiate crystallization, and cooling down to −100° C. (e.g., down to −30° C.). Diluted or saturated solutions may be used for crystallization, with or without seeding with suitable nucleating agents. Obtained crystalline solids may be purified by crystallization techniques well known in the art. Temperatures up to 100° C. may be applied to form solutions.

The salts described herein may be obtained in good yields. Re-crystallization produces purified forms suitable for use in pharmaceutical compositions. The salts may occur in more than one crystalline form. For example, some of the salts may form hydrates or solvates.

The salts described herein are especially suitable as active compounds or pro-drugs in pharmaceutical formulations to inhibit an activity of a monoamine receptor, preferably a serotonin receptor of the 5-HT2A subclass. The salts of formula IV are very soluble in aqueous systems and the free base is liberated at physiological pH ranges, providing a high bioavailability. The salts of formula IV and formula XI, in the crystalline forms disclosed herein, possess good storage stability. The crystalline compounds facilitate processing and handling for the manufacture of the salts and their formulation.

Accordingly, one embodiment is a pharmaceutical composition comprising at least one salt described herein and a pharmaceutically acceptable carrier or diluent. The amount of the salts used depends on type of formulation and desired dosages during administration time periods. The amount in an oral formulation may be from 0.1 to 500 mg, preferably from 0.5 to 300 mg, and more preferably from 1 to 100 mg.

Oral formulations may be solid formulations such as capsules, tablets, pills and troches, or liquid formulations such as aqueous suspensions, elixirs and syrups. Solid and liquid formulations encompass also incorporation of the salts into liquid or solid food. Liquids also encompass solutions of the salts for parenteral applications such as infusion or injection.

The crystalline solid salts described herein may directly be used as powder (micronized particles), granules, suspensions or solutions, or they may be combined together with other pharmaceutically acceptable ingredients in admixing the components and optionally finely divide them, and then filling capsules, composed for example from hard or soft gelatine, compressing tablets, pills or troches, or suspend or dissolve them in carriers for suspensions, elixirs, and syrups. Coatings may be applied after compression to form pills.

Pharmaceutically acceptable ingredients are well known for the various types of formulations and may be for example binders such as natural or synthetic polymers, excipients, lubricants, surfactants, sweetening and flavouring agents, coating materials, preservatives, dyes, thickeners, adjuvants, antimicrobial agents, antioxidants and carriers for the various formulation types.

Examples for binders are gum tragacanth, acacia, starch, gelatine, and biological degradable polymers such as homo- or co-polyesters of dicarboxylic acids, alkylene glycols, poly-alkylene glycols and/or aliphatic hydroxylcarboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (e.g., polyoxaethylene, polyoxapropylene and mixed polymers thereof), poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, and natural polymers like chitosan.

Examples for excipients are phosphates such as dicalcium phosphate.

Examples for lubricants are natural or synthetic oils, fats, waxes, or fatty acid salts like magnesium stearate.

Surfactants may be anionic, cationic, amphoteric, or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials are gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for antioxidants are vitamins, such as vitamin A, vitamin C, vitamin D or vitamin E, vegetable extracts or fish oils.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The pharmaceutical formulations may also contain isotonic agents, such as sugars, buffers or sodium chloride.

The salts described herein may also be formulated as effervescent tablet or powder, which disintegrate in an aqueous environment to provide a drinking solution.

A syrup or elixir may contain the salts described herein, sucrose or fructose as a sweetening agent, a preservative like methylparaben, a dye, and a flavouring agent.

Slow release formulations may also be prepared from the salts described herein in order to achieve a controlled release of the active agent in contact with the body fluids in the gastro intestinal tract, and to provide a substantial constant and effective level of the active agent in the blood plasma. Any of the compounds of formula IV to XI may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The salts described herein may also be useful for administering a combination of therapeutic agents to an animal. Such a combination therapy can be carried out in using at least one further therapeutic agent which can be additionally dispersed or dissolved in a formulation.

The salts described herein and formulations containing the salts can also be administered in combination with other therapeutic agents that are effective to treat a given condition to provide a combination therapy.

In some embodiments, the crystalline salts and the pharmaceutical composition disclosed herein are used to treat neuropsychiatric diseases including psychosis, schizophrenia, schizoaffective disorders, mania, psychotic depression, affective disorders, dementia, anxiety, sleep disorders, appetite disorders, bipolar disorder, psychosis secondary to hypertension, migraine, vasospasm, and ischemia, motor tics, tremor, psychomotor slowing, bradykinesia, and neuropathic pain. In one embodiment, the salts and compositions are used to inhibit an activity of a monoamine receptor, preferably a serotonin receptor of the 5-HT2A subclass.

Another embodiment is a method for the treatment of neurodegenerative diseases, including Parkinson's disease, Huntington's disease, Alzheimer's disease, Spinocerebellar Atrophy, Tourette's Syndrome, Friedrich's Ataxia, Machado-Joseph's disease, Lewy Body Dementia, Dystonia, Progressive Supranuclear Palsy, and Frontotemporal Dementia by administering a salt described herein.

Another embodiment is a method for treating dyskinesia associated with dopaminergic therapy, by administering a salt described herein.

Another embodiment is a method for treating dystonia, myoclonus, or tremor associated with dopaminergic therapy, by administering a salt described herein.

Another embodiment is a method for treating a thrombotic condition including myocardial infarction, thrombotic or ischemic stroke, idiopathic and thrombotic thrombocytopenic purpura, peripheral vascular disease, and Raynaud's disease, by administering a salt described herein.

Another embodiment is a method of treating addiction, including alcohol addiction, opioid addiction, and nicotine addiction, by administering a salt described herein.

Another embodiment is a method of treating a decrease in libido or ejaculatory problems by administering a salt described herein.

One embodiment includes a method of delivering a compound of formula I to a subject, comprising administering to the subject an effective amount of the salt chosen from compounds of formula IV, V, VI, VII, VIII, IX, X, or XI.

EXAMPLES

Experimental Procedures

Powder X-ray Diffraction (PXRD): PXRD was performed on a Philips 1710 powder X-ray diffractometer using CuK$_\alpha$ radiation. d-spacings were calculated from the 2θ values using the wavelength of 1.54060 Å. Generally, 2θ values were within an error of ±0.1–0.2°. The experimental error on the d-spacing values was therefore dependent on the peak location.

Differential Scanning Calorimetry (DSC): Perkin Elmer DSC 7 in gold sample pan sealed under nitrogen. Heating rate 10 K/min.

FT-Raman Spectroscopy: Bruker RFS100. Nd:YAG 1064 nm excitation, 100 mW laser power, Ge-detector, 64 scans, range 25-3500 cm$^{-1}$, cm$^{-1}$ resolution.

TG-FTIR: Thermogravimetric measurements were carried out with a Netzsch Thermo-Microbalance TG 209 coupled to a Bruker FTIR Spectrometer Vector 22 (sample pans with pinhole, nitrogen atmosphere, heating rate 10K/min).

HPLC: HPLC measurement were carried out with a HP LC1090M, Column Symmetry C18, 3.0·150 mm.

Solubility: The approximate solubility in water was determined by adding double distilled water in steps of 5 μl to 5 mg substance and sonification of the suspension for 2 minutes. The limit value of completely dissolved amount was determined. Determination of solubilities below 20 mg/l occurred with stirring suspensions in water, filtering off the excess, and measuring of the amount of substance in the filtrate.

Example 1

Preparation of N-(4-fluorobenzyl)-N-(1-methylpiperidin-4-yl)-N'-(4-(2-methylpropyloxy)phenylmethyl)carbamide a) Preparation of

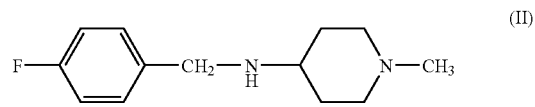

(II)

Triacetoxy borohydride (6.5 kg) was added over 1.5 h to a solution of N-methylpiperid-4-one (3.17 kg) and 4-fluorobenzylamine (3.50 kg) in methanol (30 l), maintaining the temperature under 27° C. The reaction mixture was stirred for 15 h at 22° C. The residual amine was checked by gel chromatography (4-fluorobenzylamine: <5%). A solution of 30% sodium hydroxide (12.1 kg) in water (13.6 kg) was added in 75 minutes (min) maintaining the temperature under 20° C. Methanol was distilled off to a residual volume of 26 litters. Ethyl acetate was added (26 L), the solution was stirred for 15 min, the phases were decanted over 15 min and the lower aqueous phase was discarded. Ethyl acetate was distilled under reduced pressure from the organic phase at 73-127° C. At this stage the residue was mixed with a second crude batch prepared according to this method. The combined products were then distilled at 139-140° C./20 mbar to yield 11.2 kg product (>82%).

b) Preparation of

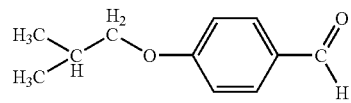

4-Hydroxybenzaldehyde (4.0 kg) and ethanol (20 l) were added to a solution of isobutyl bromide (9.0 kg) in ethanol (15 l). Potassium carbonate (13.6 kg) was added and the suspension was refluxed (74-78° C.) for 5 days. The residual 4-hydroxybenzaldehyde was checked by HPLC (<10%). The suspension was cooled to 20° C. and used in the next step.

c) Preparation of

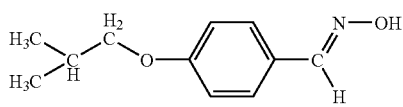

Hydroxylamine (50% in water, 8.7 kg) was added to the product from previous step b)(174 l, 176 kg) and ethanol (54 l). The suspension was refluxed (77° C.) for 3 h. Unreacted residual amounts of the compound of step b was checked by HPLC (<5%). The suspension was cooled to 30° C., filtered and the filter was washed with ethanol (54 l). The solution was concentrated by distillation under reduced pressure at 30° C. to a residual volume of 67 litters. The solution was cooled to 25° C. and water (110 l) was added. The suspension was concentrated by distillation under reduced pressure at 30° C. to a residual volume of 102 litters. Petrol ether (60-90 fraction, 96 l) was added and the mixture was heated to reflux (70° C.). The solution was cooled to 40° C. and crystallization was initiated by seeding. The suspension was cooled to 5° C. and stirred for 4 h. The product was centrifuged and the cake was washed with petrol ether (60-90 fraction, 32 l). The wet cake was dried at about 40° C. to yield 16 kg product (63%).

d) Preparation of

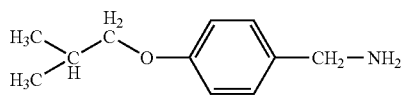

The product from previous step c) (15.7 kg) was dissolved in ethanol (123 l). Acetic acid (8.2 kg) and palladium on charcoal 5% wet (1.1 kg) were added. The oxime was hydrogenated at 22° C. and 1.5 bar for 4 h. Consumption of oxime was checked by HPLC (for information). The catalyst was filtered and the solvent was distilled under reduced pressure at 36° C. to a final volume of 31 l. Ethyl acetate (63 l) was added and the mixture was heated to reflux (75° C.) until dissolution. The solution was cooled to 45° C. and the crystallization was initiated by seeding. The suspension was cooled to 6-10° C. and stirred for 2.5 h. The product was centrifuged and the cake was washed with 2 portions of ethyl acetate (2×0.8 l). The wet cake was dried at a temperature of about 40° C. to yield 8 kg (41%).

e) Preparation of

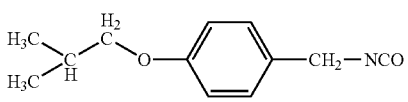

Aqueous sodium hydroxide (30%, 5.0 kg) was added to a suspension of the product from previous step d) (7.9 kg) in heptane (41 l). The solution was heated to 47° C., stirred for 15 min and decanted over 15 min. The pH was checked (pH>12) and the aqueous phase was separated. The solvent was removed by distillation under reduced pressure at 47-65° C. Heptane was added (15 l) and it was removed by distillation under reduced pressure at 58-65° C. Heptane was added (7 l), the solution was filtered and the filter was washed with heptane (7 l). The solvent was removed by distillation under reduced pressure at 28-60° C. Tetrahydrofuran (THF, 107 l) and triethylamine (TEA, 6.8 kg) were added and the temperature was fixed at 22° C. In another reactor, phosgene (5.0 kg) was introduced in tetrahydrofuran (88 l) previously cooled to −3° C. The THF and TEA solution was added to the solution of phosgene in 3 h 50 min maintaining the temperature at −3° C. The reactor was washed with tetrahydrofuran (22 l). The mixture was stirred for 45 min at 20° C. and then for 90 min at reflux (65° C.). The solvent was distilled under reduced pressure at 25-30° C. to a residual volume of 149 l. The absence of phosgene was controlled. At this stage, there still was phosgene and the suspension was degassed by bubbling nitrogen through it. After this operation the level of phosgene above the solution was below 0.075 ppm. The suspension was filtered and washed with tetrahydrofuran (30 l). The solvent was distilled under reduced pressure at 20-25° C. to a residual volume of 40 l. Tetrahydrofuran (51 l) was added and the solvent was distilled under reduced pressure at 20-25° C. to a residual volume of 40 l. The final volume was adjusted to about 52 litters by addition of tetrahydrofuran (11 l). The solution was analysed and used in the next step.

f) Preparation of the Title Compound of formula I

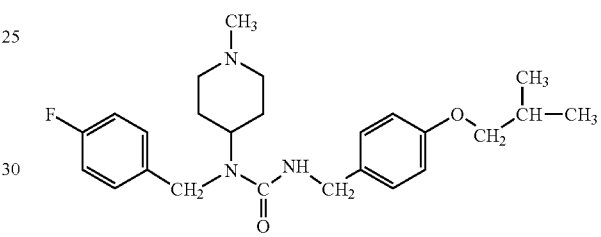

The product from previous step e) (51 l) was added in 1 h to a solution of the product from step a) (7.3 kg) in tetrahydrofuran (132 l) at 17° C. The line was washed with tetrahydrofuran (12 l) and the mixture was stirred for 15 h. Residual product from the first step was checked by HPLC. The solvent was removed by distillation under reduced pressure at 20-38° C. to a residual volume of 165 l. Charcoal (Norit SX1-G, 0.7 kg) was added, the mixture was stirred for 15 min and filtered. The line was washed with tetrahydrofuran (7 l) and the solvent was removed by distillation under reduced pressure at 20-25° C. to a residual volume of 30 l. Isopropyl acetate (96 l) was added to obtain a solution of the title compound of formula I, which contains a small amount of impurities, which were mainly side products from the previous reactions. Removal of the solvent from a sample yields a substantially amorphous solid.

g) Preparation of N-(4-fluorobenzyl)-N-(1-methylpiperidin-4-yl)-N'-(4-(2-methylpropyloxy)phenylmethyl)carbamide hemi-tartrate To the solution of the compound of Formula I in isopropyl acetate (96 l) from step f was added at 23° C. a previously prepared solution of tartaric acid (1.7 kg) in water (1.7 l) and tetrahydrofuran (23 l). The residual suspension was stirred for 2.5 days at 22° C. The tartrate crude product was centrifuged and the cake was washed with 4 portions of isopropyl acetate (4×23 l). A total of 107 kg of mother liquors was saved for later use in obtaining the tartrate salt. The wet cake was dried at about 40° C. to yield 8.3 kg (50%) product.

h) First Purification

The tartrate crude product of step g) (8.1 kg) was dissolved in demineralized water (41 l) at 22° C. Isopropyl acetate (40 L), 30% aqueous sodium hydroxide (4.3 kg) and sodium chloride (2 kg) were added. The pH was checked (>12) and the solution was stirred for 15 min. The solution was decanted over 15 min and the aqueous phase was separated. The aqueous phase was re-extracted with isopropyl acetate (12 l). Demineralized water (20 l) and sodium chloride (2.0 kg) were added to the combined organic phases, the solution was stirred for 15 min, decanted over 15 min and the aqueous phase was discarded. Charcoal (0.4 kg) was added, the mixture was stirred for 20 min and filtered. After a line wash with isopropyl acetate (12 l), the solvent was removed under reduced pressure at 20-25° C. Heptane (49 l) was added and the suspension was stirred for 15 min at 40° C. Then, 8 l of solvent was removed by distillation under reduced pressure at 38-41° C. The slurry was cooled to 20° C. and stirred for 1 h. The product was centrifuged and the cake was washed with heptane (5 l). The wet compound of Formula 1 (5.5 kg) was dissolved in ethanol (28 l) at 45° C. A solution of tartaric acid (0.72 kg) in ethanol (11 l) was added at 45° C. and the line was washed with ethanol (9 l). The solution was cooled to 43° C., seeded with the tartrate salt of the compound of Formula I, then the slurry was cooled to 35° C. in 30 min, stirred at this temperature for 1 h and cooled to −5° C. After 14 h at this temperature the product was centrifuged and washed with two portions of ethanol (2×6 l). The wet cake was dried at about 45° C. for 76 h to yield 4 kg of the hemi-tartrate.

i) Re-crystallization 150.0 g of hemi-tartrate obtained in h) was dissolved under stirring at 65° C. in 112 ml absolute ethanol and then cooled under stirring to 48° C. at a cooling rate of 1° C./min. Crystallization started after a few minutes at this temperature and the suspension turned to a thick paste within 1 h. The suspension was heated again to 60° C. and then cooled to 48° C. at a rate of 1° C./min. The obtained suspension was stirred and was cooled to 15° C. at a cooling rate of 3° C./h. The crystalline precipitate was separated by filtration and the bottle was washed with 10 ml absolute ethanol cooled to 5° C. The crystalline residue was dried under vacuum and 40° C. for 50 hours to yield 146 g crystalline pure hemi-tartrate.

j) Second Purification 15.78 g of the tartrate salt prepared from step i) was dissolved in 130 ml water. 500 ml TBME was added and the pH was adjusted to 9.8 by addition of 2 N NaOH solution. After precipitation of a white solid, the aqueous phase was extracted 5 times by 500 ml TBME. The organic phases were concentrated until a volume of about 400 ml remained. The solution was stored at 6° C. The precipitate was filtered, washed with TBME and finally dried in vacuum for 5 hours. Yield: 8.24 g of a white powder. The mother liquor was concentrated to a fourth and stored at 6° C. The precipitate was filtered and dried in vacuum for 18 hours. Yield: 1.6 g of a white powder.

PXRD revealed a crystalline compound of formula I. No Raman peaks from tartaric acid were found. The first scan of DSC (−50° C. to 210° C., 10° K/min) revealed a melting point at 123.6° C. Above about 190° C., the sample started to decompose.

Example 2

Preparation of N-(4-fluorobenzyl)-N-(1-methylpiperidin-4-yl)-N'-(4-(2-methylpropyloxy)phenylmethyl)carbamide citrate of formula IV a)

90 mg of the product from Example 1 and 40 mg citric acid were suspended in 5.0 ml ethylacetate. The suspension was stirred at 60° C. for 15 minutes (min), cooled to 23±2° C., and then stored for 30 min at 23±2° C. The precipitate was filtered off and dried in air for 30 min to yield 52 mg of a crystalline white powder. Optical microscopy shows that the obtained solid was crystalline.

b)

182 mg of the product from Example 2 and 78.4 mg citric acid were suspended in 10.0 ml ethyl acetate. The suspension was stirred at 60° C. for 30 min, then stirred at 40° C. for 90 min, and finally stirred for 60 min at 23° C. The suspension was filtered and washed with heptane, yielding 237 mg of a white crystalline powder with an endothermic peak near 153° C. (enthalpy of fusion of about 87 J/g), determined by differential scanning calorimetry at a rate of 10K/min (DSC). Thermogravimetry (TG-FTIR) showed a mass loss of about 0.7% between 60 and 160° C., which was attributed to absorbed water. Decomposition started at about 170° C. Solubility in water was about 14 mg/ml. The crystalline powder remained substantially unchanged when stored for 1 week at 60° C. and about 75% r.h. in an open container (HPLC area was 99.4% compared to reference value of 99.9%). Elemental analysis and $^1$H-NMR complies with an 1:1 stoichiometry.

The powder X-ray diffraction pattern (PXRD) of the obtained citrate salt is shown in FIG. 1 and the characteristic peaks in 2 theta with the corresponding d-spacing values in Å are given in Table 1.

TABLE 1

| d-Spacings for the compound of formula IV | | |
|---|---|---|
| Angle [°2θ] | d-spacings [Å] | Intensity (qualitative) |
| 2.8 | 31.8 | vs |
| 5.6 | 15.9 | m |
| 11.2 | 7.9 | m |
| 12.6 | 7.0 | vw |
| 12.9 | 6.9 | w |
| 14.0 | 6.3 | m |
| 14.9 | 5.96 | m |
| 15.2 | 5.83 | w |
| 16.9 | 5.23 | m |
| 17.9 | 4.94 | vw |
| 2.8 | 31.8 | vs |
| 5.6 | 15.9 | m |
| 11.2 | 7.9 | m |
| 12.6 | 7.0 | vw |
| 12.9 | 6.9 | w |
| 18.1 | 4.89 | vw |
| 18.9 | 4.68 | m |
| 19.5 | 4.56 | m |
| 21.3 | 4.17 | m |
| 21.9 | 4.05 | w |
| 22.5 | 3.95 | m |
| 22.7 | 3.91 | m |
| 23.4 | 3.79 | w |
| 24.1 | 3.70 | vw |
| 24.5 | 3.62 | vw |
| 25.5 | 3.49 | w |
| 28.5 | 3.13 | w |
| 29.9 | 2.99 | vw |
| 31.0 | 2.89 | w |

Example 3

Preparation of N-(4-fluorobenzyl)-N-(1-methylpiperidin-4-yl)-N'-(4-(2-methylpropyloxy)phenylmethyl)carbamide fumarate of formula V a)

90 mg of the product from Example 1 and 24.3 mg fumaric acid were suspended in 5.0 ml ethyl acetate. The suspension was stirred at 60° C. for 15 min, then stored for 75 min at 23±2° C. Optical microscopy revealed a crystalline substance. The suspension was filtered and washed with t-butyl methyl ether (TBME). Yield: 83 mg of a white powder. PXRD and Raman spectroscopy indicate a crystalline form A, containing amorphous parts.

The powder X-ray diffraction pattern (PXRD) is shown in FIG. 2 and the characteristic peaks in 2 theta with the corresponding d-spacing values in Å are given in Table 2.

TABLE 2 d-Spacings for the compound of formula V form A

| Angle [°2θ] | d-spacings [Å] | Intensity (qualitative) |
|---|---|---|
| 4.1 | 21.7 | m |
| 4.8 | 18.3 | s |
| 5.6 | 15.7 | s |
| 6.1 | 14.5 | s |
| 7.0 | 12.6 | s |
| 7.2 | 12.3 | m |
| 8.1 | 10.9 | w |
| 9.7 | 9.1 | w |
| 13.1 | 6.8 | w |
| 13.8 | 6.40 | w |
| 15.1 | 5.87 | w |
| 16.0 | 5.52 | m |
| 16.8 | 5.26 | m |
| 17.3 | 5.12 | w |
| 18.8 | 4.72 | s |
| 19.0 | 4.66 | s |
| 19.7 | 4.51 | m |
| 19.8 | 4.47 | s |
| 20.9 | 4.24 | m |
| 24.5 | 3.64 | m | b)

180 mg of the product from Example 2 and 48.2 mg fumaric acid were suspended in 10.0 ml ethyl acetate. The suspension was stirred at 60° C. for 30 min, then for 90 min at 40° C. and finally for 70 min at 23° C. The precipitate was filtered off and washed with heptane, yielding 167 mg of a crystalline white powder. TG-FTIR showed a mass loss of about 8.6% between 60 and 170° C., which was attributed to absorbed water, ethyl acetate and $CO_2$. Decomposition started at about 160° C. $^1$H-NMR complies with an 1:0.75 stoichiometry (base:fumaric acid). PXRD and Raman spectroscopy indicate a crystalline form B.

c)

48.6 mg of the product from Example 2 was suspended in 10.0 ml ethyl acetate. 180 mg fumaric acid was dissolved in 1 ml ethanol and added to the suspension. The resulting mixture was stirred at 50° C. for 1 hour and then at 23° C. for 21 hours. Thereafter, 12 ml ethylacetate was added and the solution was further stirred for 24 hours at 23° C. The solvent volume was reduced to half by a nitrogen flow and 9 ml heptane was then added. The formed suspension was further stirred for 24 hours at 23±2° C. The precipitate was filtered off to yield 191 mg of a crystalline white powder. PXRD and Raman spectroscopy indicate a crystalline form B. The solubility in water was >500 mg/ml. TG-FTIR shows a mass loss of about 0.9% between 70 and 140° C., which was attributed to ethyl acetate. Storage at 75% r.h. in an open container reveals changes of the substance after 3 days, detected with Raman spectroscopy. $^1$H-NMR complies with an 1:0.75 stoichiometry (base:fumaric acid). The crystalline powder remains substantially unchanged when stored for 1 week at 60° C. and about 75% r.h. in an open container (HPLC area was 96.7% compared to reference value of 99.4%). It is possible that the crystalline powder is a mixture of a fumarate and a hemi-fumarate.

The powder X-ray diffraction pattern (PXRD) is shown in FIG. 3 and the characteristic peaks in 2 theta with the corresponding d-spacing values in Å are given in Table 3.

TABLE 3 d-Spacings for the compound of formula V form B

| Angle [°2θ] | d-spacings [Å] | Intensity (qualitative) |
|---|---|---|
| 4.8 | 18.4 | vs |
| 5.6 | 15.7 | vs |
| 7.0 | 12.6 | vs |
| 8.8 | 10.0 | w |
| 9.6 | 9.2 | m |
| 10.5 | 8.4 | m |
| 10.9 | 8.1 | w |
| 11.3 | 7.8 | vw |
| 11.8 | 7.5 | w |
| 13.1 | 6.8 | m |
| 13.9 | 6.37 | m |
| 14.5 | 6.12 | m |
| 15.6 | 5.68 | m |
| 16.1 | 5.50 | vs |
| 17.3 | 5.13 | m |
| 18.0 | 4.93 | s |
| 18.9 | 4.70 | s |
| 19.7 | 4.51 | s |
| 20.2 | 4.39 | m |
| 20.6 | 4.30 | m |
| 21.3 | 4.17 | s |
| 21.9 | 4.06 | s |
| 22.9 | 3.88 | m |
| 23.3 | 3.81 | w |
| 24.3 | 3.66 | m |
| 24.4 | 3.64 | m |
| 26.1 | 3.42 | m |
| 28.7 | 3.11 | w |

Example 4

Preparation of N-(4-fluorobenzyl)-N-(1-methylpiperidin-4-yl)-N'-(4-(2-methylpropyloxy)phenylmethyl)carbamide maleate of formula VI a)

181 mg of the product from Example 1 and 48.2 mg maleic acid were dissolved in 10.0 ml ethyl acetate. The solution was stirred at 60° C. for 15 min, then for 20 min at 23±2° C. Precipitation of a white solid started after this time. The suspension was stored at 5° C. for 48 hours and then the solvent volume was reduced to a fourth by a nitrogen flow. Storage at 5° C. was continued for 72 hours. The white solid was filtered off yielding 113 mg of a crystalline powder. PXRD and Raman spectroscopy indicate a crystalline form. TG-FTIR shows a mass loss of about 7.2% between 60 and 160° C., which was attributed to absorbed water and ethyl acetate. Decomposition starts at about 160° C.

The powder X-ray diffraction pattern (PXRD) is shown in FIG. 4 and the characteristic peaks in 2 theta with the corresponding d-spacing values in Å are given in Table 4.

TABLE 4 d-Spacings for the compound of formula VI

| Angle [°2θ] | d-spacings [Å] | Intensity (qualitative) |
|---|---|---|
| 5.2 | 17.1 | w |
| 6.8 | 13.0 | vs |
| 8.9 | 10.0 | w |
| 10.3 | 8.6 | w |

TABLE 4-continued d-Spacings for the compound of formula VI

| Angle [°2θ] | d-spacings [Å] | Intensity (qualitative) |
|---|---|---|
| 11.2 | 7.9 | w |
| 12.5 | 7.1 | vw |
| 14.7 | 6.03 | vw |
| 15.5 | 5.71 | vs |
| 16.9 | 5.24 | m |
| 17.8 | 4.98 | m |
| 18.2 | 4.86 | w |
| 18.6 | 4.77 | m |
| 18.9 | 4.70 | w |
| 20.3 | 4.37 | m |
| 20.7 | 4.29 | w |
| 21.2 | 4.19 | vs |
| 21.8 | 4.08 | vw |
| 22.7 | 3.92 | w |
| 23.7 | 3.76 | w |
| 24.2 | 3.67 | w |
| 24.6 | 3.62 | m |
| 25.3 | 3.52 | w |
| 26.0 | 3.42 | vw |
| 26.3 | 3.38 | m |
| 26.8 | 3.32 | vw |
| 27.3 | 3.27 | m |
| 5.2 | 17.1 | w |
| 6.8 | 13.0 | vs |
| 8.9 | 10.0 | w |
| 28.4 | 3.14 | vw |
| 28.7 | 3.10 | w |
| 29.3 | 3.05 | m |
| 30.1 | 2.97 | w |
| 32.6 | 2.75 | w | b)

181 mg of the product from Example 2 and 48.0 mg maleic acid were dissolved in 3.0 ml acetone. The solution was stored at 5° C. for 5 days. The solvent volume was reduced to a fourth by a nitrogen flow and storage at 5° continued for 48 hours. The solvent was evaporated at ambient condition and 2 ml heptane and 100 µl acetone were added under stirring. Stirring was continued for 24 hours. The precipitated solid was filtered off to yield 182 mg of a crystalline white powder. PXRD and Raman spectroscopy indicates a crystalline maletae, which was possibly admixed with another crystalline form. TG-FTIR shows a mass loss of about 5.9% between 60 and 160° C., which was attributed to absorbed water, acetone and heptane. Decomposition started at about 170° C. $^1$H-NMR complies with an 1:1 stoichiometry. The solubility in water was >500 mg/ml.

Example 5

Preparation of N-(4-fluorobenzyl)-N-(1-methylpiperidin-4-yl)-N'-(4-(2-methylpropyloxy)phenylmethyl)carbamide malate of formula VII 181 mg of the product from Example 1 and 56.0 mg L-(–)-malic acid were suspended in 10.0 ml ethyl acetate. The suspension was stirred at 60° C. for 30 min to form a clear solution. The solution was stored at 5° C. for 1 day. The solid was filtered off from the formed suspension yielding 155 mg of a crystalline white powder. PXRD and Raman spectroscopy indicate a crystalline form A. TG-FTIR shows a mass loss of about 5.5% between 50 and 160° C., which was attributed to water and $CO_2$. Decomposition started at about 160° C. Elemental analysis and $^1$H-NMR complies with an 1:1 stoichiometry. Solubility in water was >500 mg/ml.

The powder X-ray diffraction pattern (PXRD) is shown in FIG. 5 and the characteristic peaks in 2 theta with the corresponding d-spacing values in Å are given in Table 5.

TABLE 5 d-Spacings for the compound of formula VII

| Angle [°2θ] | d-spacings [Å] | Intensity (qualitative) |
|---|---|---|
| 4.4 | 19.8 | m |
| 5.5 | 16.2 | w |
| 6.8 | 13.1 | vs |
| 7.4 | 12.0 | s |
| 10.1 | 8.8 | w |
| 10.3 | 8.6 | w |
| 11.5 | 7.7 | m |
| 12.2 | 7.2 | m |
| 14.5 | 6.1 | m |
| 15.0 | 5.92 | w |
| 16.5 | 5.35 | s |
| 17.5 | 5.05 | s |
| 18.1 | 4.89 | m |
| 18.4 | 4.83 | s |
| 18.7 | 4.75 | vs |
| 18.8 | 4.71 | vs |
| 19.2 | 4.63 | m |
| 19.5 | 4.55 | m |
| 20.3 | 4.37 | vs |
| 20.7 | 4.29 | vs |
| 21.3 | 4.17 | s |
| 22.2 | 4.00 | s |
| 22.4 | 3.97 | m |
| 23.0 | 3.87 | s |
| 23.2 | 3.83 | s |
| 23.7 | 3.75 | vw |
| 4.4 | 19.8 | m |
| 5.5 | 16.2 | w |
| 6.8 | 13.1 | vs |
| 7.4 | 12.0 | s |
| 24.7 | 3.61 | m |
| 25.0 | 3.56 | vw |
| 27.5 | 3.24 | m |
| 29.2 | 3.05 | w |
| 29.9 | 2.98 | w |
| 30.5 | 2.93 | w |

Example 6

Preparation of N-(4-fluorobenzyl)-N-(1-methylpiperidin-4-yl)-N'-(4-(2-methylpropyloxy)phenylmethyl)carbamide phosphate of formula VIII 181 mg of the product from Example 1 was dissolved in 3 ml 2-propanol. 842 µl phosphoric acid (0.5. molar) was added and a clear solution was formed. The sample was stored for at 5° C. for 1 day. The precipitate was filtered off and dried in vacuum for 15 hours. Yield was 60 mg of white crystalline powder. PXRD and Raman spectroscopy indicate a crystalline form A. TG-FTIR shows a mass loss of about 3.9% between 80 and 160° C., which was attributed to 2-propanol. Decomposition started at about 170° C. $^1$H-NMR complies with an 1:1 stoichiometry. Solubility in water was >250 mg/ml.

The powder X-ray diffraction pattern (PXRD) is shown in FIG. 6 and the characteristic peaks in 2 theta with the corresponding d-spacing values in Å are given in Table 6.

TABLE 6 d-Spacings for the compound of formula VIII

| Angle [°2θ] | d-spacings [Å] | Intensity (qualitative) |
|---|---|---|
| 5.1 | 17.3 | vs |
| 8.7 | 10.1 | m |
| 10.0 | 8.9 | m |
| 13.3 | 6.7 | w |
| 13.7 | 6.5 | m |
| 15.0 | 5.91 | s |
| 15.4 | 5.74 | m |
| 16.3 | 5.44 | vw |
| 17.2 | 5.16 | w |
| 18.0 | 4.93 | m |
| 18.5 | 4.80 | m |
| 18.7 | 4.75 | w |
| 19.4 | 4.56 | m |
| 20.8 | 4.27 | m |
| 21.5 | 4.14 | m |
| 23.0 | 3.86 | m |
| 23.5 | 3.78 | vw |
| 25.0 | 3.55 | m |
| 30.9 | 2.89 | w |

Example 7

Preparation of N-(4-fluorobenzyl)-N-(1-methylpiperidin-4-yl)-N'-(4-(2-methylpropyloxy)phenylmethyl)carbamide succinate of formula IX a)
90 mg of the product from Example 1 and 24.7 mg succinic acid were suspended in 5.0 ml ethyl acetate. The mixture was stirred at 60° C. for 15 min forming a clear solution. The solution was stored for 30 min at 23±2° C. and then cooled to 5° C. Precipitation occurs after 30 min. The suspension was stored for 16 hours at 5° C. and the precipitate was filtered off, washed with TBME and heptane to yield 55 mg of a crystalline white solid. PXRD and Raman spectroscopy indicate a crystalline form.

b)
179 mg of the product from Example 1 and 48.9 mg succinic acid were suspended in 10.0 ml ethyl acetate. The mixture was stirred at 60° C. for 15 min forming a clear solution. The solution was stored for 40 min at 23±2° C. and then cooled to 5° C. Precipitation occurs after 30 min. The suspension was stirred for 1 hour at 23° C. and the precipitate was filtered off, washed with heptane to yield 147 mg of a crystalline white powder. PXRD and Raman spectroscopy indicate a crystalline form. TG-FTIR shows a mass loss of about 18.8% between 60 and 250° C., which was attributed to mostly $CO_2$ and water. Elemental analysis indicates the formation of a dihydrate. $^1$H-NMR complies with an 1:1 stoichiometry. Solubility in water was >500 mg/ml.
The powder X-ray diffraction pattern (PXRD) is shown in FIG. 7 and the characteristic peaks in 2 theta with the corresponding d-spacing values in Å are given in table 7.

TABLE 7 d-Spacings for the compound of formula IX

| Angle [°2θ] | d-spacings [Å] | Intensity (qualitative) |
|---|---|---|
| 5.4 | 16.7 | vw |
| 6.9 | 12.8 | vs |
| 10.3 | 8.6 | w |

TABLE 7-continued d-Spacings for the compound of formula IX

| Angle [°2θ] | d-spacings [Å] | Intensity (qualitative) |
|---|---|---|
| 11.6 | 7.6 | m |
| 13.8 | 6.4 | w |
| 16.1 | 5.51 | s |
| 16.8 | 5.27 | w |
| 17.1 | 5.19 | m |
| 17.7 | 5.00 | vw |
| 18.5 | 4.79 | m |
| 19.1 | 4.65 | vw |
| 19.4 | 4.58 | vw |
| 20.1 | 4.42 | w |
| 20.5 | 4.32 | m |
| 21.4 | 4.16 | s |
| 21.9 | 4.05 | s |
| 22.7 | 3.91 | m |
| 23.2 | 3.83 | vw |
| 24.1 | 3.69 | w |
| 24.7 | 3.60 | vw |
| 26.3 | 3.38 | vw |
| 26.9 | 3.31 | w |
| 27.3 | 3.27 | w |
| 5.4 | 16.7 | vw |
| 6.9 | 12.8 | vs |
| 10.3 | 8.6 | w |
| 11.6 | 7.6 | m |
| 13.8 | 6.4 | w |
| 28.0 | 3.19 | vw |
| 28.4 | 3.14 | w |
| 30.1 | 2.97 | w |
| 32.4 | 2.76 | w |
| 33.6 | 2.66 | w |
| 34.1 | 2.62 | w |

Example 8

Preparation of N-(4-fluorobenzyl)-N-(1-methylpiperidin-4-yl)-N'-(4-(2-methylpropyloxy)phenylmethyl)carbamide sulphate of formula X 180 mg of the product from Example 1 was dissolved in 5 ml ethanol. 842 μl sulphuric acid (0.5 molar) was added and the formed clear solution was stored at 5° C. for 48 hours. The solvent was evaporated by a nitrogen flow. The solid residue was suspended in 3 ml TBME and 0.1 ml ethanol and the suspension was stirred for 17 hours at 23±2° C. Filtration yields 80 mg of a crystalline white powder. PXRD and Raman spectroscopy indicate a crystalline form.
The powder X-ray diffraction pattern (PXRD) is shown in FIG. 8 and the characteristic peaks in 2 theta with the corresponding d-spacing values in Å are given in table 8.

TABLE 8 d-Spacings for the compound of formula X

| Angle [°2θ] | d-spacings [Å] | Intensity (qualitative) |
|---|---|---|
| 2.9 | 30.8 | w |
| 5.2 | 17.0 | vs |
| 9.2 | 9.6 | m |
| 10.7 | 8.3 | w |
| 11.5 | 7.7 | vw |
| 13.1 | 6.8 | m |
| 13.9 | 6.4 | m |
| 16.1 | 5.49 | vs |
| 16.7 | 5.29 | w |
| 18.5 | 4.79 | s |
| 19.1 | 4.65 | m |
| 19.6 | 4.53 | s |

TABLE 8-continued d-Spacings for the compound of formula X

| Angle [°2θ] | d-spacings [Å] | Intensity (qualitative) |
|---|---|---|
| 20.1 | 4.42 | m |
| 20.6 | 4.30 | vs |
| 21.2 | 4.18 | m |
| 21.4 | 4.15 | s |
| 22.0 | 4.04 | m |
| 22.9 | 3.89 | w |
| 24.7 | 3.60 | m |
| 25.0 | 3.56 | w |
| 26.3 | 3.38 | vw |
| 27.0 | 3.30 | w |
| 28.0 | 3.19 | vw |
| 28.5 | 3.13 | vw |
| 29.2 | 3.05 | vw |
| 31.6 | 2.83 | vw |
| 32.7 | 2.74 | w |

Example 9

Preparation of N-(4-fluorobenzyl)-N-(1-methylpiperidin-4-yl)-N'-(4-(2-methylpropyloxy)phenylmethyl)carbamide edisylate of formula XI 180 mg of the product from Example 1 was dissolved in 2 ml dioxane and a solution of 48 mg 1,2-ethane disulphonic acid dihydrate in 4 ml dioxane was then added. The solution was stored at 8° C. for 10 days. The precipitated solid was filtered off to yield 206 mg of a crystalline white powder. PXRD and Raman spectroscopy indicate a crystalline form. TG-FTIR shows a mass loss of about 1.2% between 60 and 160° C., which was attributed to dioxane. Decomposition starts at about 170° C. Elemental analysis indicates a 2:1 stoichiometry (compound of formula I: 1,2-ethane disulphonic acid. $^1$H-NMR complies with both a 2:1 or a 1:1 stoichiometry. Solubility in water was 4 mg/ml. The crystalline powder remains a white powder when stored for 1 week at 60° C. and about 75% r.h. in a closed container (HPLC area was 97.4% compared to reference value of 96.8%). Storage for 1 week at 100° C. in a closed ampoule does not decompose the crystalline product and the white powder remains substantially unchanged (HPLC area 97.4%).

The powder X-ray diffraction pattern (PXRD) is shown in FIG. 9 and the characteristic peaks in 2 theta with the corresponding d-spacing values in Å are given in table 9.

TABLE 9 d-Spacings for the compound of formula XI

| Angle [°2θ] | d-spacings [Å] | Intensity (qualitative) |
|---|---|---|
| 7.3 | 12.1 | m |
| 8.1 | 10.9 | vw |
| 8.9 | 10.0 | s |
| 9.5 | 9.3 | m |
| 10.9 | 8.1 | m |
| 13.3 | 6.6 | m |
| 14.1 | 6.3 | vw |
| 14.6 | 6.05 | vs |
| 16.7 | 5.31 | s |
| 17.1 | 5.18 | m |
| 17.8 | 4.97 | vs |
| 18.4 | 4.81 | w |
| 18.9 | 4.68 | s |
| 19.4 | 4.57 | m |
| 19.9 | 4.46 | m |

TABLE 9-continued d-Spacings for the compound of formula XI

| Angle [°2θ] | d-spacings [Å] | Intensity (qualitative) |
|---|---|---|
| 20.4 | 4.35 | m |
| 20.8 | 4.26 | s |
| 21.5 | 4.12 | s |
| 21.9 | 4.05 | vw |
| 22.5 | 3.96 | m |
| 22.9 | 3.88 | w |
| 23.7 | 3.75 | m |
| 24.6 | 3.62 | m |
| 25.2 | 3.53 | w |
| 25.6 | 3.48 | m |
| 26.0 | 3.42 | w |
| 26.9 | 3.31 | m |
| 28.3 | 3.15 | w |
| 29.1 | 3.07 | w |
| 29.6 | 3.01 | vw |
| 35.9 | 2.49 | w |

What is claimed is:

1. An isolated and purified crystalline salt of N-(4-fluorobenzyl)-N-(1-methylpiperidin-4-yl)-N'-(4-(2-methylpropyloxy)phenylmethyl)carbamide of formula I,

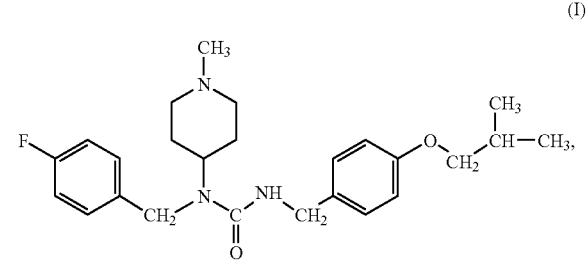

(I)

wherein the salt is the citrate or edisylate salt.

2. The salt of claim 1, wherein the salt is a citrate.

3. The salt of claim 2 that exhibits a X-ray powder diffraction pattern comprising peaks having d-values in angstroms of about 31.8, about 15.9, about 7.9, about 6.3, about 5.96, about 5.23, and about 4.68.

4. The salt of claim 1, wherein the salt is an edisylate (ethanedisulfonate).

5. The salt of claim 4 that exhibits a X-ray powder diffraction pattern comprising peaks having d-values in angstroms of about 10.0, about 6.05, about 5.31, about 4.97, about 4.26, and about 4.12.

6. A crystalline salt of N-(4-fluorobenzyl)-N-(1-methylpiperidin-4-yl)-N'-(4-(2-methylpropyloxy)phenylmethyl)carbamide of formula I,

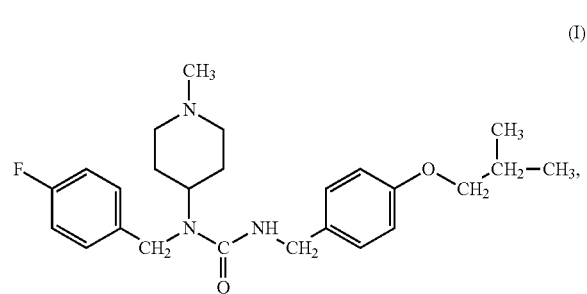

(I)

produced by a process comprising:
  a) forming a solution of the compound of formula I in an organic solvent;
  b) adding citric acid or 1,2-ethane disulfonic acid to said solution; and
  c) isolating the salt.

7. A pharmaceutical composition comprising one or more salts of claim 1 and a pharmaceutically acceptable carrier.

8. The phatinaceutical composition of claim 7, wherein the composition is in a solid dosage form.

9. The pharmaceutical composition of claim 8, wherein the solid dosage form is suitable for oral administration.

10. The pharmaceutical composition of claim 9, wherein the amount of the salt of formula IV is from about 1 to 100 mg.

11. The salt of claim 2 that exhibits a X-ray powder diffraction pattern comprising peaks having d-values in angstroms of about 15.9, about 7.9, about 6.3, and about 4.68.

12. The salt of claim 4 that exhibits a X-ray powder diffraction pattern comprising peaks having d-values in angstroms of about 10.0, about 6.05, and about 4.97.

13. The citrate salt of claim 2, wherein the salt is of formula IV:

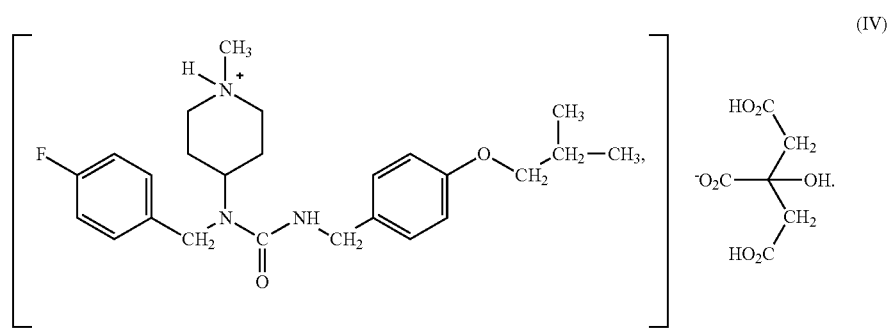

14. The edisylate salt of claim 4, wherein the salt is of formula XI:

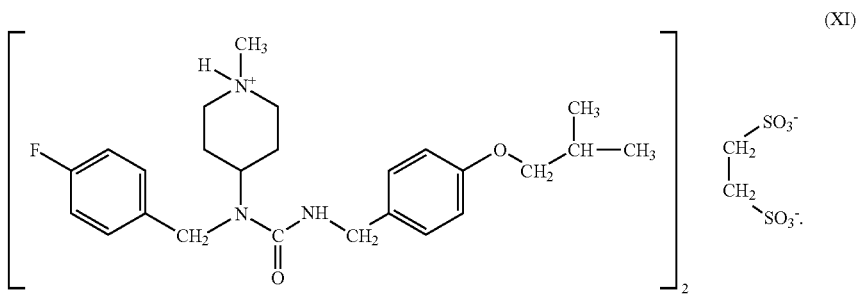

15. The citrate salt of claim 2, wherein the salt has a water solubility of about 14 mg/mL.

16. The edisylate salt of claim 4, wherein the salt has a water solubility of about 4 mg/mL.

* * * * *